United States Patent
Yamamoto

(10) Patent No.: US 9,198,959 B2
(45) Date of Patent: Dec. 1, 2015

(54) ADENOVIRUS VACCINE VECTOR AND METHODS OF USE

(75) Inventor: Masato Yamamoto, Golden Valley, MN (US)

(73) Assignee: Regents of The University of Minnesota, St. Paul, MN (US)

(*) Notice: Subject to any disclaimer, the term of this patent is extended or adjusted under 35 U.S.C. 154(b) by 0 days.

(21) Appl. No.: 13/402,618

(22) Filed: Feb. 22, 2012

(65) Prior Publication Data

US 2012/0213828 A1 Aug. 23, 2012

Related U.S. Application Data

(60) Provisional application No. 61/445,239, filed on Feb. 22, 2011.

(51) Int. Cl.
| | |
|---|---|
| C12N 15/00 | (2006.01) |
| A61K 39/00 | (2006.01) |
| A61K 9/00 | (2006.01) |
| A61K 39/35 | (2006.01) |
| C12N 15/86 | (2006.01) |

(52) U.S. Cl.
CPC ........... *A61K 39/0011* (2013.01); *A61K 9/0019* (2013.01); *A61K 39/0008* (2013.01); *A61K 39/35* (2013.01); *C12N 15/86* (2013.01); *A61K 2039/542* (2013.01); *A61K 2039/55566* (2013.01); *C12N 2710/10343* (2013.01)

(58) Field of Classification Search
CPC ............. A61K 2039/542; C12N 15/86; C12N 2710/10343
See application file for complete search history.

(56) References Cited

U.S. PATENT DOCUMENTS

| | | | | |
|---|---|---|---|---|
| 2002/0187128 | A1* | 12/2002 | Imperiale | 424/93.2 |
| 2003/0148520 | A1* | 8/2003 | Yu et al. | 435/456 |
| 2004/0203133 | A1* | 10/2004 | Ehrhardt et al. | 435/235.1 |
| 2005/0042217 | A1* | 2/2005 | Qi et al. | 424/144.1 |
| 2005/0232900 | A1* | 10/2005 | Vogels et al. | 424/93.2 |
| 2007/0269410 | A1* | 11/2007 | Tucker | 424/93.2 |

OTHER PUBLICATIONS

Anderson et al. Gene Therapy 2000 7:1034-1038.*
Albinsson et al. "Adenovirus type 41 lacks an RGD alpha(v)-integrin binding motif on the penton base and undergoes delayed uptake in A549 cells." 1999. *Virus Res*; 64:125-136.
Bowles et al. "Specific aspects of gastro-intestinal transit in children for drug delivery design." 2010. *Int J Pharm*. 395:37-43.
Brandt et al. "Mast cells are required for experimental oral allergen-induced diarrhea." 2003. *J. Clin. Invest*. 112(11):1666-1677.
Corbett et al. "Induction and Chemotherapeutic Response of Two Transplantable Ductal Adenocarcinomas of the Pancreas in C57BL/6 Mice." 1984. *Cancer Res*. 44(2):717-726.
de Jong et al. "Candidate adenoviruses 40 and 41: fastidious adenoviruses from human infant stool." 1983. *J Med Virol*; 11:215-231.
De Magistris. "Mucosal delivery of vaccine antigens and its advantages in pediatrics." 2006. *Adv Drug Deliv Rev*; 58:52-67.
Fallaux et al. "Characterization of 911: a new helper cell line for the titration and propagation of early region 1-deleted adenoviral vectors." 1996. *Hum Gene Ther*. 7:215-222.
Fehervari et al. "The Mucosa: at the frontlines of immunity." 2008. *Trends Immunol*. 29:503-504.
Green et al. "Transvascular flux and tissue accrual of Evans blue: effects of endotoxin and histamine." 1998. *J. Lab. Clin. Med*. 111:173-183.
Holmgren et al. "Mucosal Immunity and Vaccines." 2005. *Nat Med*. 11:S45-53.
Hubatsch et al. "Determination of drug permeability and prediction of drug absorption in Caco-2 monolayers." 2007. *Nat Protoc*; 2:2111-2119.
Kernéis et al. "Conversion by Peyer's Patch lymphocytes of human enterocytes into M cells that transport bacteria." 1997. *Science*. 277:949-952.
Kidd et al. "Adenovirus type 40 virions contain two distinct fibers." 1993. *Virology*; 192:73-84.
Kiyono et al. "NALT—versus Peyer's-Patch-mediated mucosal immunity." 2004. *Nat Rev Immunol*; 4:699-710.
Lange et al. "Evans blue permeation of intestinal mucosa in the rat." 1994. *Scand. J. Gastroenterol*. 29(1):38-46.
Lefrançois et al. "Isolation of mouse small intestinal intraepithelial lymphocytes, Peyer's Patch, and lamina propria cells." 1996. *Curr Protoc Immunol*. 3.19.1-3.19.16.
Liu et al. "An E1B-19 kDa gene deletion mutant adenovirus demonstrates tumor necrosis factor-enhanced cancer selectivity and enhanced oncolytic potency." 2004. *Mol Ther*. 9:786-803.
Luo et al. "A protocol for rapid generation of recombinant adenoviruses using the AdEasy system." 2007. *Nat Protoc*. 2:1236-1247.
Mautner et al. "Properties of the adenovirus type 40 E1B promoter that contribute to its low transcriptional activity." 1999. *Virology*. 265:10-19.
Mercier et al. "Oral immunization of rhesus macaques with adenoviral HIV vaccines using enteric-coated capsules." 2007. *Vaccine*. 25:8687-8701.
Mestecky et al. "Oral immunization: an update." 2008. *Curr Opin Gastroenterol*; 24:713-719.
Miura et al. "Direct selection of targeted adenovirus vectors by random peptide display on the fiber knob." 2007. *Gene Ther*. 14(20):1448-1460.
Mowat, Anatomical basis of tolerance and immunity to intestinal antigens. 2003. *Nat Rev Immunol*; 3:331-341.
Nakamura et al. "Reduction of natural adenovirus tropism to the liver by both ablation of fiber-coxsackievirus and adenovirus receptor interaction and use of replaceable short fiber." 2003. *J Virol*. 77:2512-2521.

(Continued)

*Primary Examiner* — Brian Whiteman
(74) *Attorney, Agent, or Firm* — Mueting, Raasch & Gebhardt. P.A.

(57) ABSTRACT

Ad40-based polynucleotides, viral vectors, methods of making such polynucleotides and viral vectors, pharmaceutical compositions that includes such polynucleotides and viral vectors, and uses of such compositions are disclosed herein. Generally, the Ad40-based polynucleotide includes an Ad40-based vector that includes a genetic modification that decreases expression of an E1 coding region and a heterologous polynucleotide.

9 Claims, 18 Drawing Sheets
(1 of 18 Drawing Sheet(s) Filed in Color)

(56) References Cited

OTHER PUBLICATIONS

Neutra et al. "Mucosal Vaccines: the promise and the challenge." 2006. *Nat Rev Immunol.* 6:148-158.

Neutra et al. "Antigen sampling across epithelial barriers and induction of mucosal immune responses." 1996. *Annu Rev Immunol.* 14:275-300.

Pringle et al. "Detection of plasmid DNA vectors following gene transfer to the murine airways." 2005. *Gene Ther.* 12:1206-1214.

Roy et al. "Oral gene delivery with chitosan-DNA nanoparticles generates immunologic protection in a murine model of peanut allergy" 1999. *Nat Med* 5:387-391.

Thomas et al. "A real-time PCR method to rapidly titer adenovirus stocks." 2007. *Methods Mol Med.* 130:185-192.

Tiemessen et al. "The subgroup F adenoviruses" 1995. *J Gen Virol.* 76:481-497.

Tiemessen et al. "Adenovirus type 40 and 41 growth in vitro: host range diversity reflected by differences in patterns of DNA replication." 1994. *J Virol.* 68:1239-1244.

Tyrer et al. "Validation and quantitation of an in vitro M-cell model." 2002. *Biochem Biophys Res Commun.* 299:377-383.

Uhnoo et al. "Importance of enteric adenoviruses 40 and 41 in acute gastroenteritis in infants and young children." 1984. *J Clin Microbiol.* 20:365-372.

Wang et al. "Delivery of human immunodeficiency virus vaccine vectors to the intestine induces enhanced mucosal cellular immunity." 2009. *J Virol.* 83:7166-7175.

Weiss et al. "Rapid inactivation of rotaviruses by exposure to acid buffer or acidic gastric juice." 1985. *J Gen Virol.* 66:2725-2730.

Worbs et al. "Oral tolerance originates in the intestinal immune system and relies on antigen carriage by dendritic cells." 2006. *J. Exp. Med.* 203(3):519-527.

Yamasaki et al. "Development of a method for an effective amplification of human adenovirus 40." 2010. *Arch Virol;* 155:1059-1068.

Zhang et al. "Defining the in vivo function of Siglec-F, a CD33 Siglec expressed on mouse eosinophils." 2007. *Blood.* 109(10):4280-4287.

* cited by examiner

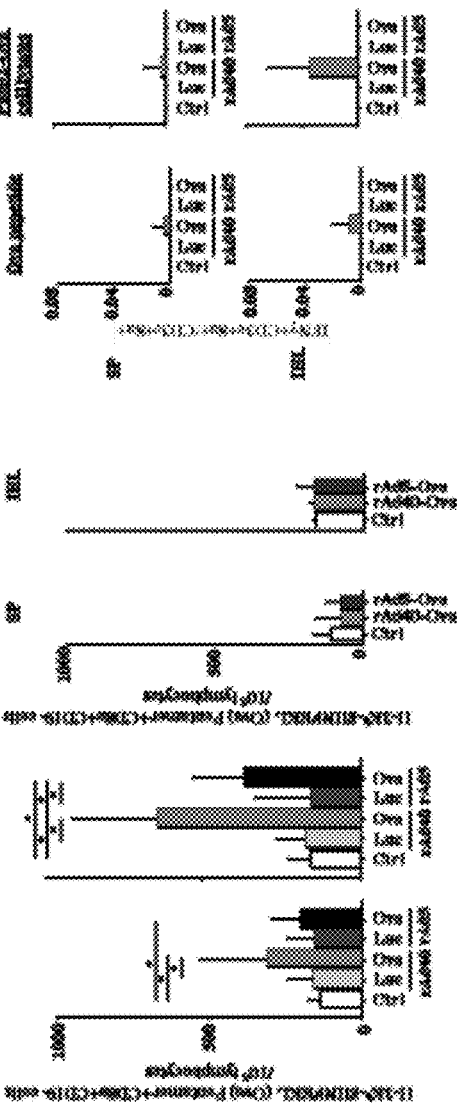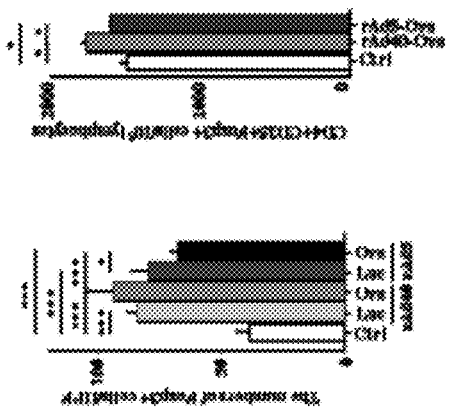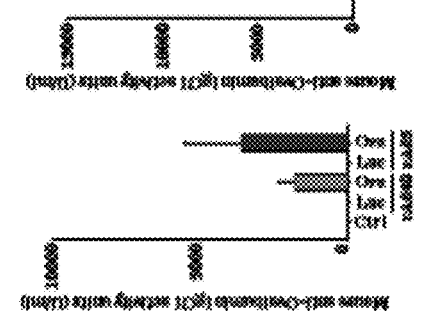

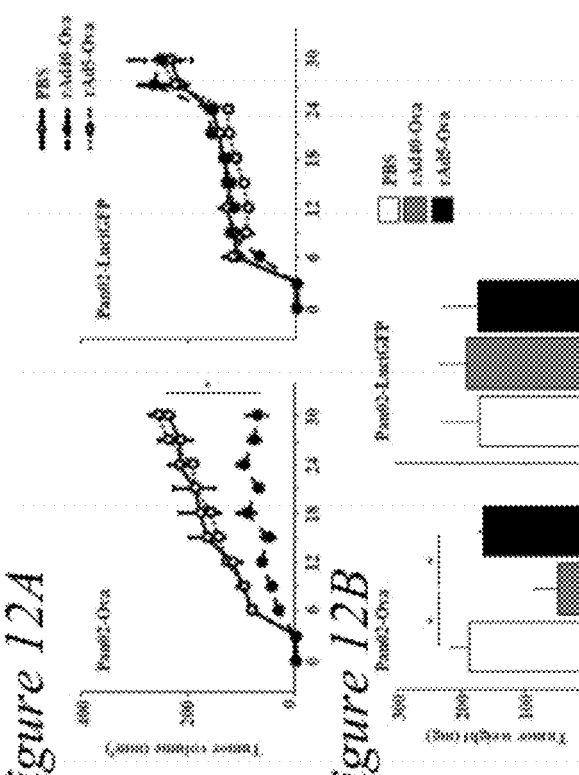
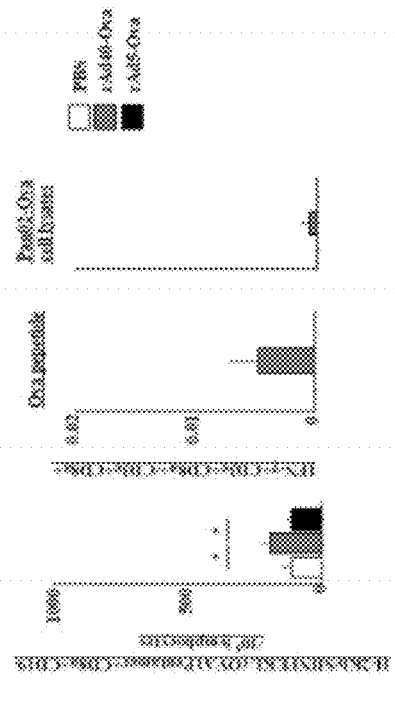
Figure 12A
Figure 12B
Figure 12C
Figure 12D

```
                        SEQUENCE LISTING

<160> NUMBER OF SEQ ID NOS: 23

<210> SEQ ID NO 1
<211> LENGTH: 20
<212> TYPE: DNA
<213> ORGANISM: artificial
<220> FEATURE:
<223> OTHER INFORMATION: synthetic oligonucleotide primer

<400> SEQUENCE: 1
actcttgagt gcgagcgagt                                             20

<210> SEQ ID NO 2
<211> LENGTH: 21
<212> TYPE: DNA
<213> ORGANISM: artificial
<220> FEATURE:
<223> OTHER INFORMATION: synthetic oligonucleotide primer

<400> SEQUENCE: 2
ttaatcctca tcgctggatt c                                           21

<210> SEQ ID NO 3
<211> LENGTH: 18
<212> TYPE: DNA
<213> ORGANISM: artificial
<220> FEATURE:
<223> OTHER INFORMATION: synthetic oligonucleotide primer

<400> SEQUENCE: 3
atggagcgcc caaactca                                               18

<210> SEQ ID NO 4
<211> LENGTH: 20
<212> TYPE: DNA
<213> ORGANISM: artificial
<220> FEATURE:
<223> OTHER INFORMATION: synthetic oligonucleotide primer

<400> SEQUENCE: 4
gtcattgggg tcatttacgg                                             20

<210> SEQ ID NO 5
<211> LENGTH: 20
<212> TYPE: DNA
<213> ORGANISM: artificial
<220> FEATURE:
<223> OTHER INFORMATION: synthetic oligonucleotide primer

<400> SEQUENCE: 5
ttcctgcgct aacgtaacct                                             20

<210> SEQ ID NO 6
<211> LENGTH: 20
<212> TYPE: DNA
<213> ORGANISM: artificial
<220> FEATURE:
```

```
<223> OTHER INFORMATION: synthetic oligonucleotide primer

<400> SEQUENCE: 6
taaagcctaa cgctccggta                                              20

<210> SEQ ID NO 7
<211> LENGTH: 20
<212> TYPE: DNA
<213> ORGANISM: artificial
<220> FEATURE:
<223> OTHER INFORMATION: synthetic oligonucleotide primer

<400> SEQUENCE: 7
tgacttcaac cccgtctacc                                              20

<210> SEQ ID NO 8
<211> LENGTH: 20
<212> TYPE: DNA
<213> ORGANISM: artificial
<220> FEATURE:
<223> OTHER INFORMATION: synthetic oligonucleotide primer

<400> SEQUENCE: 8
gggggctaga aaacaaaacc                                              20

<210> SEQ ID NO 9
<211> LENGTH: 23
<212> TYPE: DNA
<213> ORGANISM: artificial
<220> FEATURE:
<223> OTHER INFORMATION: synthetic oligonucleotide primer

<400> SEQUENCE: 9
aactttctct cttaatagac gcc                                          23

<210> SEQ ID NO 10
<211> LENGTH: 19
<212> TYPE: DNA
<213> ORGANISM: artificial
<220> FEATURE:
<223> OTHER INFORMATION: synthetic oligonucleotide primer

<400> SEQUENCE: 10
agggggctag aaacaaaa                                                19

<210> SEQ ID NO 11
<211> LENGTH: 20
<212> TYPE: DNA
<213> ORGANISM: artificial
<220> FEATURE:
<223> OTHER INFORMATION: synthetic oligonucleotide primer

<400> SEQUENCE: 11
cgtgtcacct gcagttcatt                                              20

<210> SEQ ID NO 12
<211> LENGTH: 20
<212> TYPE: DNA
<213> ORGANISM: artificial
<220> FEATURE:
<223> OTHER INFORMATION: synthetic oligonucleotide primer

<400> SEQUENCE: 12
cctgagcccc tgatgtttta                                              20
```

-continued

```
<210> SEQ ID NO 13
<211> LENGTH: 20
<212> TYPE: DNA
<213> ORGANISM: artificial
<220> FEATURE:
<223> OTHER INFORMATION: synthetic oligonucleotide primer

<400> SEQUENCE: 13
aaactcaggc acaaccatcc                                                 20

<210> SEQ ID NO 14
<211> LENGTH: 20
<212> TYPE: DNA
<213> ORGANISM: artificial
<220> FEATURE:
<223> OTHER INFORMATION: synthetic oligonucleotide primer

<400> SEQUENCE: 14
accttttgat gccactacgg                                                 20

<210> SEQ ID NO 15
<211> LENGTH: 25
<212> TYPE: DNA
<213> ORGANISM: artificial
<220> FEATURE:
<223> OTHER INFORMATION: synthetic oligonucleotide primer

<400> SEQUENCE: 15
ccgcctgaag tctctgatta agtac                                           25

<210> SEQ ID NO 16
<211> LENGTH: 21
<212> TYPE: DNA
<213> ORGANISM: artificial
<220> FEATURE:
<223> OTHER INFORMATION: synthetic oligonucleotide primer

<400> SEQUENCE: 16
tggagcaaga tggattccaa t                                               21

<210> SEQ ID NO 17
<211> LENGTH: 20
<212> TYPE: DNA
<213> ORGANISM: artificial
<220> FEATURE:
<223> OTHER INFORMATION: synthetic oligonucleotide primer

<400> SEQUENCE: 17
ccagaacatc atccctgcat                                                 20

<210> SEQ ID NO 18
<211> LENGTH: 21
<212> TYPE: DNA
<213> ORGANISM: artificial
<220> FEATURE:
<223> OTHER INFORMATION: synthetic oligonucleotide primer

<400> SEQUENCE: 18
gttcagctct gggatgacct t                                               21

<210> SEQ ID NO 19
<211> LENGTH: 21
<212> TYPE: DNA
<213> ORGANISM: artificial
<220> FEATURE:
<223> OTHER INFORMATION: synthetic oligonucleotide primer
```

```
<400> SEQUENCE: 19
gcagtcaggg aggttctgag g                                              21

<210> SEQ ID NO 20
<211> LENGTH: 21
<212> TYPE: DNA
<213> ORGANISM: artificial
<220> FEATURE:
<223> OTHER INFORMATION: synthetic oligonucleotide primer

<400> SEQUENCE: 20
ggtggagact gaccacttcg a                                              21

<210> SEQ ID NO 21
<211> LENGTH: 25
<212> TYPE: DNA
<213> ORGANISM: artificial
<220> FEATURE:
<223> OTHER INFORMATION: synthetic oligonucleotide primer

<400> SEQUENCE: 21
ggtgctgagt atgtcgtgga gtcta                                          25

<210> SEQ ID NO 22
<211> LENGTH: 20
<212> TYPE: DNA
<213> ORGANISM: artificial
<220> FEATURE:
<223> OTHER INFORMATION: synthetic oligonucleotide primer

<400> SEQUENCE: 22
cggagatgat gacccgtttg                                                20

<210> SEQ ID NO 23
<211> LENGTH: 7
<212> TYPE: PRT
<213> ORGANISM: artificial
<220> FEATURE:
<223> OTHER INFORMATION: ovalbumin (OVA) H-2Kb epitope

<400> SEQUENCE: 23

Ser Ile Ile Asn Phe Lys Leu
1               5
```

ADENOVIRUS VACCINE VECTOR AND METHODS OF USE

CROSS-REFERENCE TO RELATED APPLICATION

This application claims priority to U.S. Provisional Patent Application Ser. No. 61/445,239 filed Feb. 22, 2011.

GOVERNMENT FUNDING

This invention was made with government support under 1RO1 CA094084 awarded by the NIH/NCI. The government has certain rights in the invention.

SUMMARY OF THE INVENTION

The present invention relates to polynucleotides and Ad40-based viral vectors, and also to methods relating to the production and use of such polynucleotides and viral vectors, including methods for treating certain medical conditions.

Thus, in one aspect, the invention provides a genetically modified genetically modified polynucleotide. Generally, the polynucleotide includes an Ad40-based polynucleotide that includes a genetic modification that decreases expression of an E1 coding region, and a heterologous polynucleotide. In some cases, the genetic modification can include, for example, a deletion of at least a portion of the E1 coding region or a deletion of a regulatory polynucleotide sequence that, when present, is required for expression of the E1 coding region.

In some embodiments, the heterologous polynucleotide can include, for example, a polynucleotide that encodes an interfering polynucleotide, a polynucleotide that encodes a therapeutic polypeptide, or a polynucleotide that encodes a prophylactic polypeptide. Generally, the interfering polynucleotide can interfere with production of a polypeptide associated with a medical condition. Generally, a therapeutic polypeptide or a prophylactic polypeptide can be a polypeptide effective for treating a medical condition such as, for example, a cancer, an infectious disease, or an inflammatory disease.

In another aspect, the invention provides an Ad40-based viral vector that includes a genetically modified polynucleotide as summarized above.

In another aspect, the invention provides a composition that generally includes the genetically modified polynucleotide summarized above and a pharmaceutically acceptable carrier. In some embodiments, the genetically modified polynucleotide may be provided as a portion of an Ad40-based viral vector as summarized above. In some embodiments, the composition can further include an enteric coating.

In another aspect, the invention provides a method of making the genetically modified polynucleotide summarized above. Generally, the method includes modifying an Ad40 polynucleotide to decrease expression of an E1 coding region, and introducing a heterologous polynucleotide into the Ad40 polynucleotide. In some embodiments, modifying the Ad40 polynucleotide can include deleting at least a portion of the E1 coding region or deleting at least a portion of a regulatory polynucleotide sequence that, if present, is required for expression of the E1 coding region. In some of these embodiments, the heterologous polynucleotide may be introduced at the site of the deletion.

In yet another aspect, the invention provides methods of treating certain medical conditions. Generally, the method includes administering to a subject in need of such treatment the composition summarized above. In some embodiments, the composition may be administered orally. In other embodiments, the composition may be administered intraduodenally.

In some embodiments, the composition may be administered so that the genetically modified polynucleotide localizes in cells in the Peyer's patch, cells of the colon, cells of mesenteric lymph nodes, or cells of the spleen.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent with color drawings) will be provided by the Office upon request and payment of the necessary fee.

and Ad5-CMV-Luc (Ad5). (e) luciferase activity in in vitro M cell model. Ad40pΔE1-Luc (Ad40, non-CMV); pAd40pΔE1-CMV-Luc (Ad40, CMV); Ad5-CMV-Luc (Ad5, CMV). (f) luciferase activity in in vitro M cell model, after a pepsin treatment using Ad40pΔE1-CMV-Luc (Ad40) and Ad5-CMV-Luc (Ad5). Error bars indicate the 95% confidence interval. Asterisks denote statistical significance (P<0.05). RLU, relative luminescence units.

FIG. 5. In vivo biodistribution of luciferase-expressing Ad40-based vectors and Ad5-based vectors following oral and intraduodenal administration. (a) The relative copy numbers of luciferase reporter DNA (luciferase reporter DNA per murine GAPDH DNA) at 48 hours after oral administration. (b) The luciferase copy number at 48 hours after intraduodenal administration. The results shown are mean values with each experiment having been repeated three independent times and each experiment conducted in triplicate. Error bars indicate the 95% confidence interval. Asterisks and double asterisks denote statistical significance (P<0.05 and <0.01, respectively). C, control; 40, Ad40pΔE1-CMV-Luc; 5, Ad5-CMV-Luc.

Figure 6A:
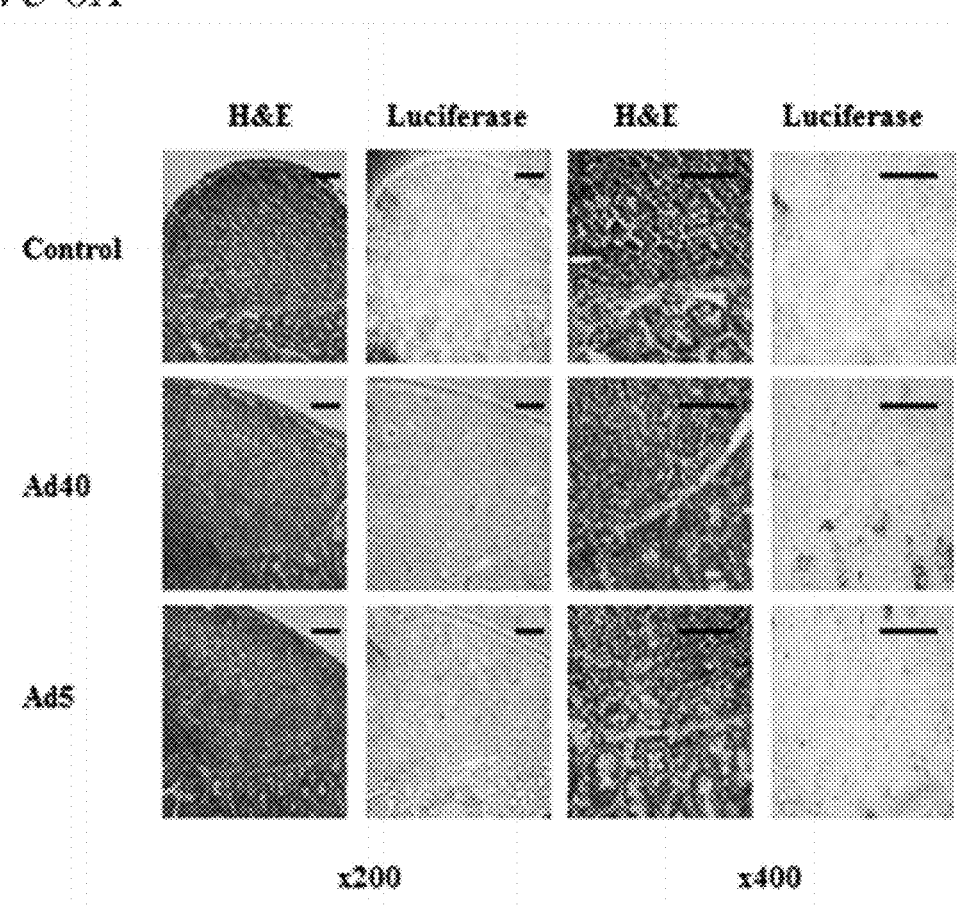
Figure 6B:
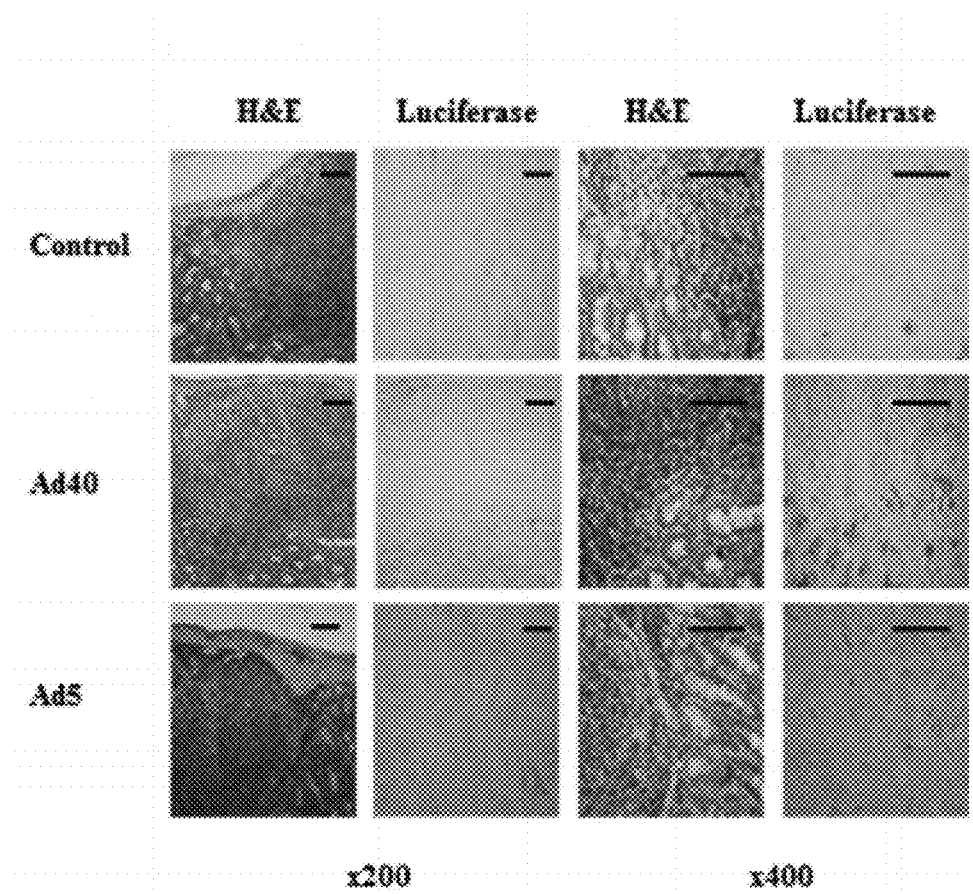

FIG. 6. Immunohistochemistry for detection of luciferase reporter protein in murine ileum around Peyer's patches' domes following oral or intraduodenal administration with a luciferase-expressing Ad40-based vector or a luciferase-expressing Ad5-based vector. (a) Luciferase expression was detected in the ileum of Ad40pΔE1-CMV-Luc (Ad40) and Ad5-CMV-Luc (Ad5) injected C57BL/6 mice at 48 hours after oral administration. (b) Luciferase expression was observed in the ileum of Ad40pΔE1-CMV-Luc (Ad40) and Ad5-CMV-Luc (Ad5) injected C57BL/6 mice at 48 hours after intraduodenal administration. (c) luciferase expression (red) in mouse ileum around PPs' domes at 48 hours after intraduodenal administration with rAd40pΔE1-CMV-Luc (rAd40) and rAd5-CMV-Luc (rAd5) detected by immunofluorescence (IF), stained for nuclei (DAPI) and CD11c. The panels in the right column are magnifications of the boxed area immediately to its left. Bar=100 μm. H & E, hematoxylin and eosin staining; Ctrl, control. The pictures shown are representative of two independent experiments (magnification, ×200 and ×400). Bar=100 μm. H&E, hematoxylin and eosin staining; Ad40, Ad40pΔE1-CMV-Luc; Ad5, Ad5-CMV-Luc.

Figure 7:
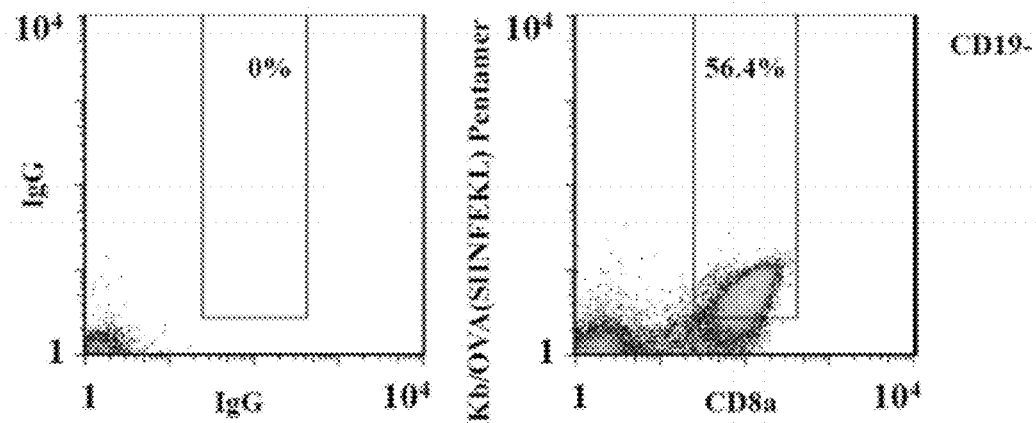

FIG. 7. Staining of Ova-specific cytotoxic T lymphocytes (CTL) in Ad40-Ova immunized mice.

FIG. 8 Mucosal and systemic immune responses induced by a single intraduodenal administration of Ad vectors in B6 mice. (a-b) The number of H-2K$^b$-SIINFEKL (Ova)-specific CD8a+CD19− cells in the spleen (SP) or liver (intrahepatic lymphocyte, IHL) (a) 14 days after intraduodenal administration with control (Ctrl), rAd40pΔE1-CMV-Luc (rAd40-Luc), rAd40pΔE1-CMV-Ova (rAd40-Ova), rAd5-CMV-Luc (rAd5-Luc), or rAd5-CMV-Ova (rAd5-Ova) and (b) 42 days after intraduodenal administration with control (Ctrl), rAd40-Ova, or rAd5-Ova. (c) The ratio of interferon-γ (IFN-γ)-secreting Ova peptide- or Pan02-Ova cell lysates-specific CD8+ T cells to CD8+ T cells in the spleen and liver at 14 days after intraduodenal administration with control, rAd40-Luc, rAd40-Ova, rAd5-Luc, or rAd5-Ova. (d) The number of Foxp3+ cells in MLNs at 14 days after intraduodenal administration with control, rAd40-Luc, rAd40-Ova, rAd5-Luc, or rAd5-Ova. (e) The number of the CD4+CD25+Foxp3+ Tregs in MLNs at 42 days after intraduodenal administration with control, rAd40-Ova, or rAd5-Ova. (f) The activities of Ova-specific IgG1 in serum at 14 days after intraduodenal administration with control, rAd40-Luc, rAd40-Ova, rAd5-Luc, or rAd5-Ova. (g) The activities of Ova-specific IgG1 in serum at 0, 7, 14, 21, 28, 35, and 42 days after intraduodenal administration with control, rAd40-Ova, or rAd5-Ova.

FIG. 9. Delayed-type hypersensitivity responses. (a) Time line illustrating B6 mice immunized with a subcutaneous administration of Ova plus complete Freund's adjuvant (CFA) at 28 days after intraduodenal administration with control, rAd40-Ova, or rAd5-Ova. Fourteen days (42 days after intraduodenal administration) after Ova immunization, a footpad was challenged with Ova subcutaneous and swelling was measured at 48 hours and 72 hours after subcutaneous Ova challenge. (b) The diameter of the footpad swelling in control (Ctrl) and rAd40-Ova-pretreated or rAd5-Ova-pretreated mice measured at 48 hours and 72 hours after subcutaneous challenge. (c) Splenic IFN-γ-secreting Ova-specific CD8+ or CD4+ T cells at seven days after subcutaneous challenge (49 days after intraduodenal administration).

FIG. 10. Mouse model of ovalbumin-induced diarrhea. (a) BALB/c mice were sensitized by an intraperitoneal administration of Ova plus aluminum potassium sulfate adjuvant (alum) at 28 days and 42 days after intraduodenal administration with control, rAd40-Ova, or rAd5-Ova, and challenged with intragastric administration of Ova every two days at 56 days after intraduodenal administration. (b) Diarrhea occurrence assessed for one hour after intragastric Ova challenge in control (Ctrl) and rAd40-Ova-pretreated or rAd5-Ova-pretreated mice. (c) Plasma histamine levels after one hour following the ninth intragastric challenge. (d) Ova-specific plasma IgG1, IgG2a and IgE, and fecal IgA after one hour following the ninth intragastric challenge.

FIG. 11. Systemic anaphylaxis models. (a) BALB/c mice were sensitized by an intraperitoneal administration of Ova plus alum at 28 days and 42 days after the intraduodenal administration with control (Ctrl), rAd40-Ova, or rAd5-Ova, and challenged with nine intragastric administrations of Ova at 56 days after intraduodenal administration and an intravenous Ova challenge at 74 days. (b) Symptom score in control and rAd40-Ova- or rAd5-Ova-pretreated mice. (c) Plasma histamine levels 15 minutes after intravenous challenge. (d) Macroscopic view of cecum and colon 60 minutes after intravenous challenge. White arrows indicate solid stool pellets. (e-f) Intestinal vascular permeabilities (e), and eosinophil counts of bone marrow (f) 60 minutes after intravenous challenge. WBCs, white blood cells.

FIG. 12. Protection against tumor growth induced by a single intravenous administration in mouse subcutaneous pancreatic cancer models. (a) Mice at 14 days after intravenous administration with PBS, rAd40-Ova, or rAd5-Ova were subcutaneously implanted with either 5×10$^5$ Pan02-Ova cells, which express Ova, or Pan02-LuciGFP cells, which lack Ova. Tumor progression was measured by calliper every three days for up to 30 days after tumor inoculation and is represented as the product of the two largest perpendicular diameters (mm$^2$). (b) Tumors were excised at 30 days after tumor inoculation, and weighed for statistical analysis. The antitumor immunity against Ova-expressing tumor mediated by rAd40-Ova was essential to Ova-directed antigens. (c-d) Splenocytes were extracted at 30 days after tumor inoculation (Pan02-Ova, c; Pan02-LuciGFP, d). The number of H-2K$^b$-SIINFEKL (Ova)-specific CD8a+CD19− cells in the spleen of PBS-pretreated, rAd40-Ova-pretreated, or rAd5-Ova-pretreated mice and the ratio of Ova peptide-specific or Pan02-Ova cell lysates-specific IFN-γ-secreting CD8+ T cells to CD8+ T cells in the spleen were measured by flow cytometry. Functional Pan02-Ova-specific systemic CTL immunity was modulated only by rAd40-Ova. Ova peptide-specific CTLs did not represent the antitumor systemic immunity.

FIG. 13. Protection against tumor growth induced by a single intravenous administration with rAd40 expressing mouse mesothelin in mouse orthotopic pancreatic cancer models. (A) The kinetic growth of Pan02-LuciGFP tumors was monitored every week by live animal imaging using bioluminescence imaging. (B) Quantitation of luminescence signals generated by the Pan02-LuciGFP tumors in (A). Data show a mean bioluminescent flux of three mice in each group (error bars represent 95% CI). Regions of interest (ROIs) are marked with red circles. (C) Macroscopic views at 29 days after tumor inoculation of Pan02-LuciGFP into the pancreas of PBS-pretreated, rAd40-Ova-pretreated, or rAd40-Msln-pretreated mice. Shaded arrows indicate Pan02-LuciGFP tumor in the pancreas. White arrows indicate intestinal obstruction. (D) IL-6 plasma levels at 29 days after tumor inoculation of Pan02-LuciGFP into the pancreas of PBS-pretreated, rAd40-Ova-pretreated, or rAd40-Msln-pretreated mice.

Figure 14:
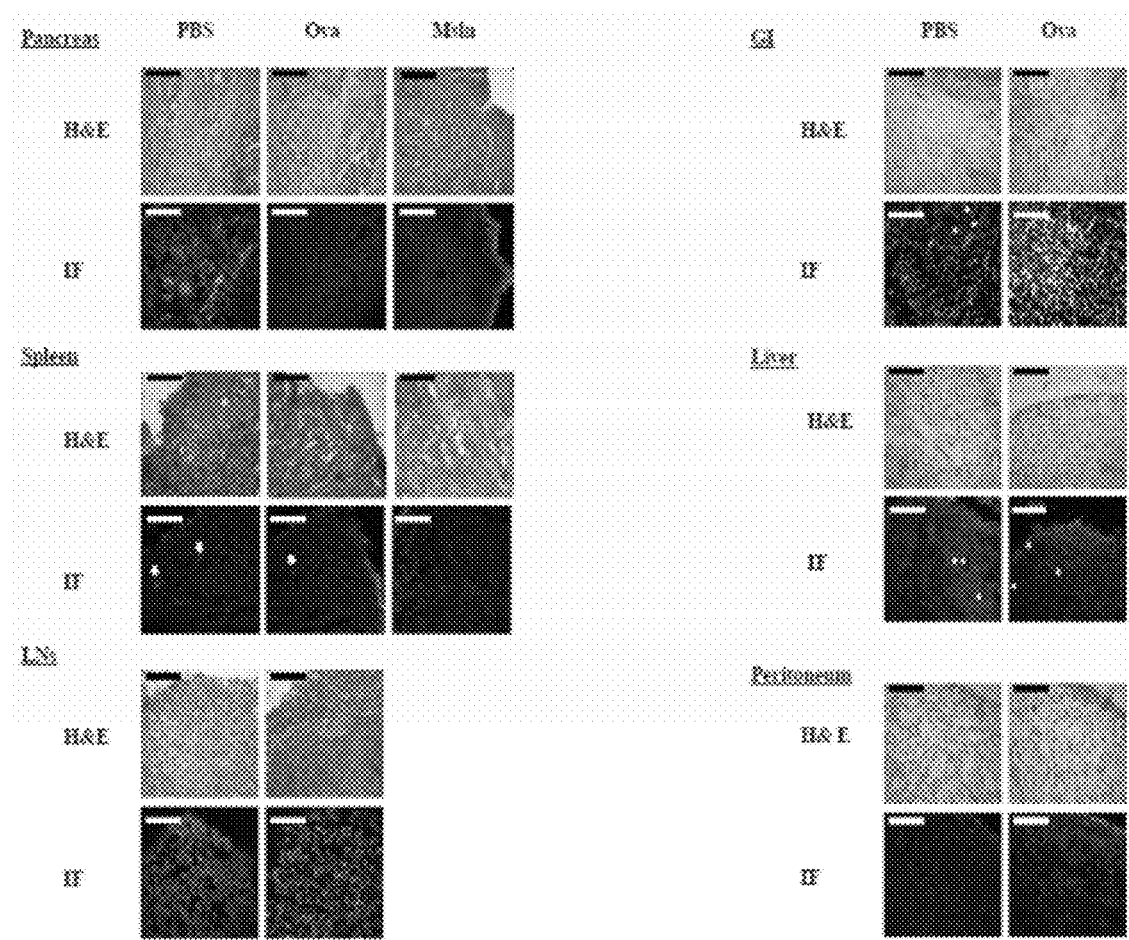
Figure 15A:
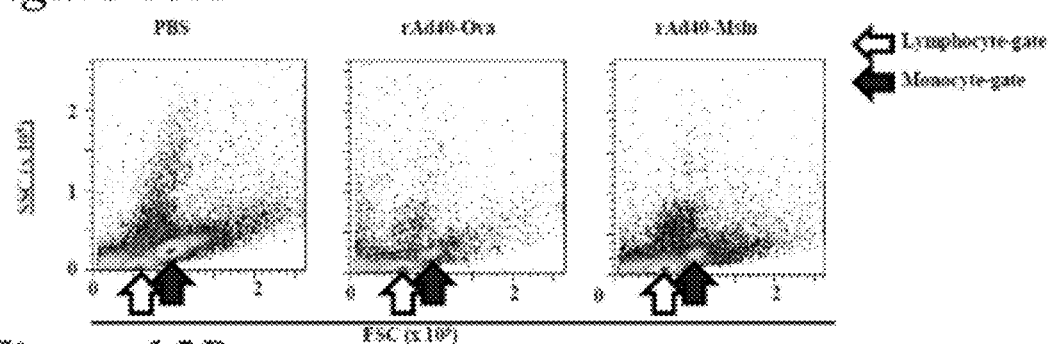
Figure 15B:
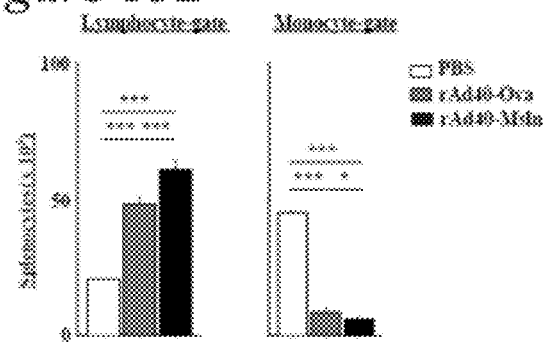
Figure 15C:
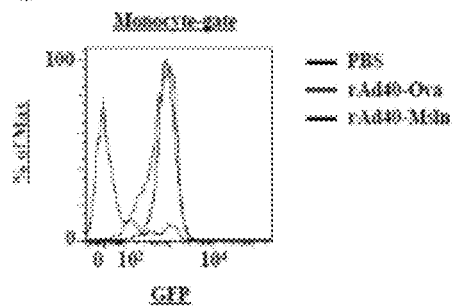
Figure 15D:
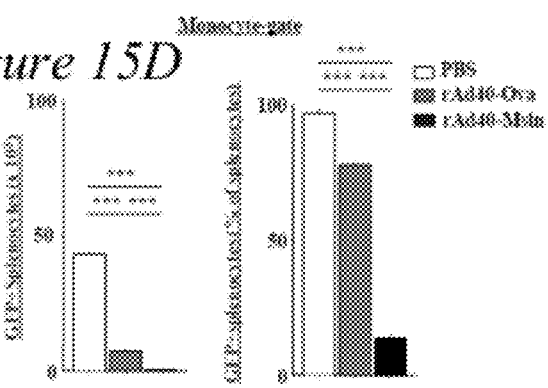

FIG. 14. Preventive mesothelin expression induced by a single intravenous administration with rAd40 expressing mouse mesothelin in mouse orthotopic pancreatic cancer models. Msln protein expression in tumor at 29 days after tumor inoculation detected by immunofluorescence stained for nuclei (DAPI) and observed for GFP. Msln protein expression was observed in pancreas of PBS-pretreated mice, and in metastatic diseases (i.e., spleen, liver, gastrointestinal tract (GI), lymph nodes (LNs), and peritoneum) of PBS-treated and rAd40-Ova-treated mice. White arrows indicate Msln+/DAPI+/GFP+triple-positive cells. Msln protein is not expressed in any Pan02-LuciGFP tumors of rAd40-Msln-pretreated mice. Bar=100 µm. H & E, hematoxylin and eosin staining; Ova, rAd40-Ova; Msln, rAd40-Msln.

FIG. 15. Preventive splenic tumor growth induced by a single intravenous administration with rAd40 expressing mouse mesothelin in mouse orthotopic pancreatic cancer models. (A and B) Increased number of splenocytes in the monocyte-gate at 29 days after tumor inoculation of Pan02-LuciGFP into the pancreas of PBS-pretreated, rAd40-Ova-pretreated, or rAd40-Msln-pretreated mice. Splenocytes were prepared for flow cytometry and shown at FSC/SSC dot-plots (A). White arrows indicate the lymphocyte-gate. Black arrows indicate the monocyte-gate. Shown are representative quantitative evaluation on the numbers of splenocytes in both lymphocyte- and monocyte-gates (B). (C and D) Preventive splenic Pan02-LuciGFP growth induced by intravenous rAd40-Msln. Shown are representative histogram (C) and quantitative evaluation (D).

FIG. 16. Systemic immune responses induced by a single intravenous administration with rAd40 expressing mouse mesothelin. (A) The ratio of Pan02-Msln cell lysates-specific IFN-γ-secreting CD8+ T cells to CD8+ T cell, IFN-γ-secreting CD4+ T cells to CD4+ T cell or IFN-γ-secreting NK1.1+ T cells to NK1.1+ T cells in the spleen at 14 days after intravenous administration with PBS, rAd40-Luc, rAd40-Ova, or rAd40-Msln. (B) Mice at 14 days after intravenous administration with PBS, rAd40-Ova, or rAd40-Msln were implanted with $2.5 \times 10^5$ Pan02-LuciGFP into the pancreas. At 29 days after tumor inoculation, mice were sacrificed and splenocytes were extracted for FCM. The ratio of Pan02-Msln cell lysates-specific IFN-γ-secreting CD8+ T cells to CD8+ T cell, or Pan02-LuciGFP cell lysates-specific IFN-γ-secreting CD8+ T cells to CD8+ T cell or IL-10-secreting CD4+ T cells to CD4+ T cells in the spleen was measured by flow cytometry.

DETAILED DESCRIPTION OF ILLUSTRATIVE EMBODIMENTS

We report herein the construction of a vector suitable for delivery of a therapeutic and/or prophylactic polynucleotide. The vectors are based on the adenovirus Ad40. Present adenovirus-based vectors require specific cell lines in order to provide efficient, large-scale replication. The vectors described herein overcome that technical deficiency of existing adenovirus-based vectors. The vector described herein possesses a genetic modification that decreases expression of an E1 coding region (e.g., a deletion) and, therefore, permits large-scale production of the vector in a broader range of eukaryotic cell types.

The vector can exhibit tropism toward cells of the gastrointestinal (GI) tract and, therefore, may be particularly suited for delivery of prophylactic and/or therapeutic polynucleotides effective for treating intestinal conditions and/or inducing a mucosal immune response.

As used herein, the following terms shall have the indicated meanings:

"Ad40-based" refers to a polynucleotide or a viral vector that includes (a) native Ad40 components such as, for example, native Ad40 nucleotide sequences or, in the case of a viral vactor, native Ad40 viral proteins, and (b) at least one genetically-engineered heterologous component. In this context, the "genetically engineered" character of the component may be satisfied merely by being heterologous to Ad40 and recombined into the Ad40-based polynucleotide or viral vector.

"Express" and variations thereof refer to the conversion of genetic information in a nucleotide sequence to a gene product. Expression of a nucleotide sequence (e.g., a coding region of DNA) may be measured and/or described with reference to (a) transcription of DNA to mRNA, (b) translation of mRNA to protein, (c) post-translational steps (e.g., modification of the primary amino acid sequence; addition of a carbohydrate, a lipid, a nucleotide, or other moiety to the protein; assembly of subunits; insertion of a membrane-associated protein into a biological membrane; and the like), or any combination of the foregoing.

"Interfering polynucleotide" and variations thereof refer to a polynucleotide that decreases expression of a particular target coding region. While an interfering polynucleotide may be characterized as decreasing expression of a particular coding region or the encoded polypeptide, the specific target of interference may be a portion of the translated region of an mRNA or a portion of an untranslated region of the mRNA. Thus, an interfering polynucleotide can include, for example, a small interfering RNA (siRNA), a microRNA (miRNA), antisense DNA, etc.

"Decrease expression" and variations thereof refer to any measurable decrease in expression of a coding region of interest. For example, decreasing expression of a specified protein can refer to decreasing production of the protein. As another example, inhibition of a nucleotide sequence can refer to a decrease in transcription of (e.g., a coding sequence) or from (e.g., a regulatory sequence such as a promoter) the nucleotide sequence. The extent of inhibition may be characterized as a percentage of a normal level of activity.

"Heterologous" refers to a polynucleotide or polypeptide that is experimentally added to an Ad40 polynucleotide or viral particle, respectively.

"Polynucleotide" refers to a sequence of two or more nucleotide bases without regard to the length of the sequence. A polynucleotide can be single stranded or double stranded, and can include one or more DNA bases and/or one or more RNA bases.

"Polypeptide" refers to a sequence of amino acid residues without regard to the length of the sequence. Therefore, the term "polypeptide" refers to any amino acid sequence having at least two amino acids and includes full-length proteins and, as the case may be, polyproteins.

"Prophylactic" and variations thereof refer to a treatment that limits, to any extent, the development and/or appearance of a symptom or clinical sign of a condition.

"Therapeutic" and variations thereof refer to a treatment that ameliorates one or more existing symptoms or clinical signs associated with a condition.

"Treat" or variations thereof refer to reducing, limiting progression, ameliorating, or resolving, to any extent, the symptoms or signs related to a condition. "Ameliorate" and variations thereof refer to any reduction in the extent, severity, frequency, and/or likelihood of a symptom or clinical sign characteristic of a particular condition. "Sign" or "clinical sign" refers to an objective physical finding relating to a particular condition capable of being found by one other than the patient. "Symptom" refers to any subjective evidence of disease or of a patient's condition.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Although mucosal immune responses may be efficiently induced by administering a vaccine, vaccines are commonly administered intramuscularly or subcutaneously—i.e., to non-mucosal tissues. In contrast, oral vaccination may induce substantial mucosal antibody responses in the small intestine, ascending colon, mammary glands, and salivary glands, and ensure the timely and regular boosting of immunity without using needle and syringe. The intestinal immune system represents a large component of the immune system. However, the intestinal immune system is often insufficiently stimulated by intramuscular and/or subcutaneous vaccinations due to the separation of mucosal and systemic immune systems in the absence of direct initiation of intestinal mucosa. Only a few mucosal vaccines—e.g., rotavirus, Salmonella typhi, cholera, and poliovirus—are available for oral immunization.

Peyer's patches (PPs) are lymphoid nodules located in the ileum and are involved in initiating mucosal immunity and tolerance. Microfold cells (M cells), which are located in the follicle-associated epithelium of PPs, transport antigens and microorganisms. Therefore, developing an oral delivery system that targets the intestinal mucosa, especially intestinal M cell and PPs, may improve the efficacy of vaccine.

The human adenovirus serotype 40 (Ad40) possesses mucosal tropism in the gastrointestinal (GI) tract. Ad40-based gene transfer vectors may therefore be suitable for oral vaccination targeting the intestinal mucosa. Although Ad40 is considered a fastidious virus because it had been difficult to culture in vitro compared to other adenoviruses, we have established a replication method for Ad40 and found Ad40 mutants that possess a partially deleted E1 region.

We report generating Ad40-based vectors and compare their in vitro and in vivo characteristics with those of a standard Ad5-based vector for targeting the intestinal mucosa, especially intestinal M cell and PPs. Our results indicate that an Ad40-based vector can be an effective delivery system to intestinal mucosa.

Targeting of Intestinal Mucosa by Luciferase Expression Vectors In Vitro.

Table 1 shows differences in titers obtained using different Ad vectors. The viral particle (VP) titers of luciferase expression vectors were all in the same order of magnitude. However, the Ad vector titer of CMV promoter-driven luciferase-reporter-gene-expressing Ad5-based vector (Ad5-CMV-Luc), measured both in terms of plaque forming units (PFUs) and tissue culture infectious dose 50 ($TCID_{50}$) assays, was 10-fold and 1000-fold higher than those of Ad40pΔE1-Luc and Ad40pΔE1-CMV-Luc, respectively.

TABLE 1

Titers of luciferase-reporter-gene-expressing adenovirus vectors.

| | Ad40ΔE1-Luc | Ad40ΔE1-CMV-Luc | Ad5-CMV-Luc |
|---|---|---|---|
| VP/mL | $7.18 \times 10^{11}$ | $3.86 \times 10^{11}$ | $5.20 \times 10^{11}$ |
| PFU/mL | $1.02 \times 10^{8a}$ | $1.60 \times 10^{6}$ | $1.25 \times 10^{9}$ |
| | (0.96-1.08) | (1.45-1.75) | (0.42-1.67) |
| $TCID_{50}$/mL | $1.25 \times 10^{8}$ | $1.99 \times 10^{6}$ | $1.99 \times 10^{9}$ |
| | (1.15-1.34) | (1.39-2.58) | (1.18-2.80) |

$^a$The median (interquartile range) of three independent experiments are shown.
VP, viral particle;
PFU, plaque forming unit;
$TCID_{50}$, tissue culture infectious dose 50.

Figure 3A:
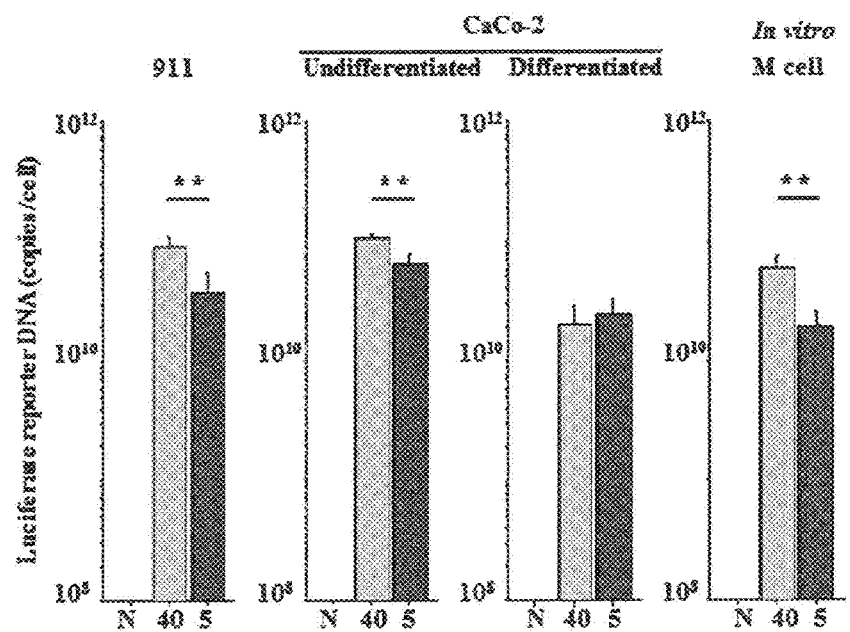
FIG. 3. Ad vector binding assay comparing Ad40pΔE1-Luc-based vector and Ad5-based vector. (a) without pepsin treatment. (b) after pepsin treatment. The isolated DNA was analyzed by real-time PCR analysis to determine the luciferase reporter DNA copy number. The results shown are mean values with each experiment having been repeated three independent times and each experiment conducted in triplicate. Error bars indicate the 95% confidence interval. Asterisks and double asterisks denote statistical significance ($P<0.01$ and $<0.001$, respectively). N, no virus; 40, Ad40pΔE1-Luc; 5, Ad5-CMV-Luc.
Figure 3B:
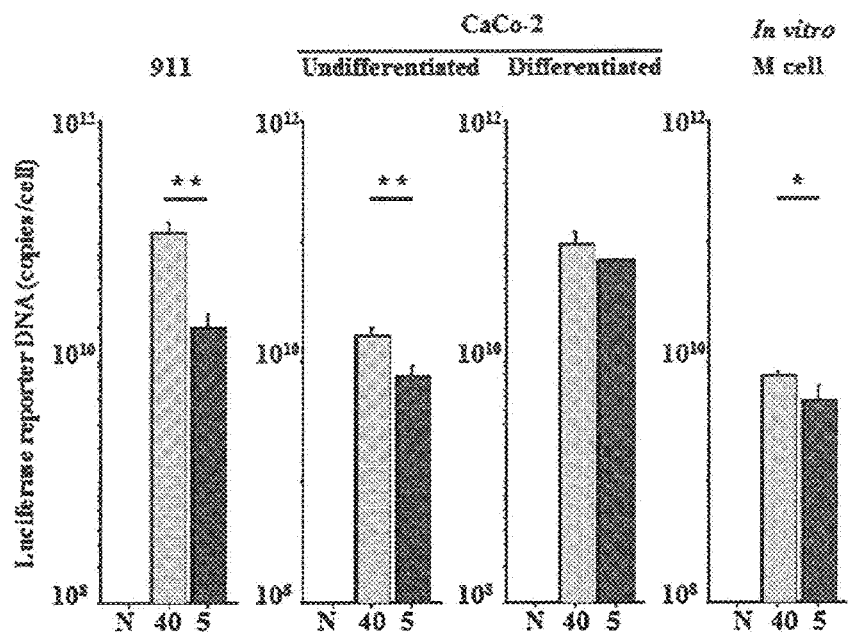

To evaluate the effects of gastric fluid, we used vectors treated with HCl and pepsin for five minutes at 37° C. FIG. 3a shows in vitro binding of Ad40pΔE1-Luc and Ad5-CMV-Luc. The copy numbers of luciferase reporter DNA in 911 cells, undifferentiated CaCo-2 cells, and an in vitro M cell model with Ad40pΔE1-Luc is significantly higher than those of Ad5-CMV-Luc. Results were similar after pepsin treatment (FIG. 3b).

Figure 4A:
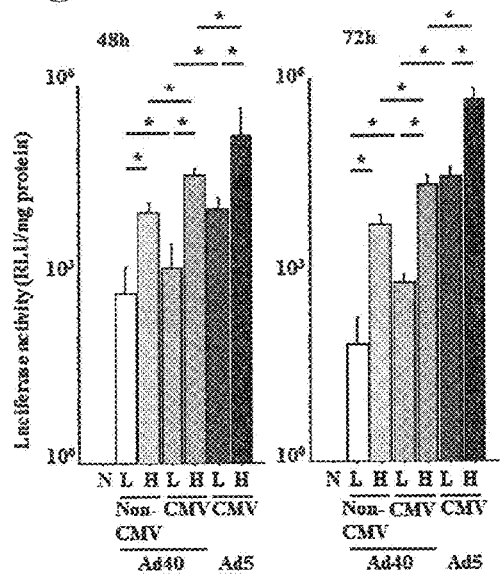
FIG. 4. Luciferase-reporter-gene-expressing Ad40-based vector with and without a pepsin treatment can transduce luciferase expression in CaCo-2 cells and human M cell models in vitro. (a) luciferase activity in undifferentiated CaCo-2 cells. After 24 hours, cells were infected with 0 (N, no virus), or 200 VP/cell (L, low), or 2000 (H, high) VP/cell and incubated for 48 hours or 72 hours at 37° C. Ad40pΔE1-Luc (Ad40, non-CMV); pAd40pΔE1-CMV-Luc (Ad40, CMV); Ad5-CMV-Luc (Ad5, CMV). (b) luciferase activity in undifferentiated CaCo-2, after a pepsin treatment using Ad40pΔE1-CMV-Luc (Ad40) and Ad5-CMV-Luc (Ad5). (c) luciferase activity in differentiated CaCo-2 cells. After 24 hours, cells were infected with 0 (N, no virus), or 200 VP/cell (L, low), or 2000 (H, high) VP/cell and incubated for 48 hours or 72 hours at 37° C. Ad40pΔE1-Luc (Ad40, non-CMV); pAd40pΔE1-CMV-Luc (Ad40, CMV); Ad5-CMV-Luc (Ad5, CMV). (d) luciferase activity in differentiated CaCo-2, after a pepsin treatment using Ad40pΔE1-CMV-Luc (Ad40)
Figure 4B:
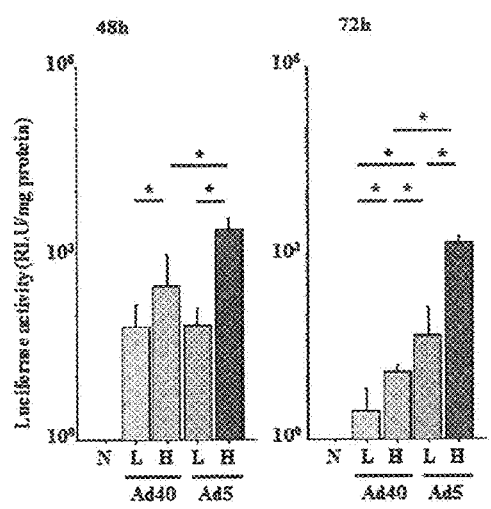
Figure 4C:
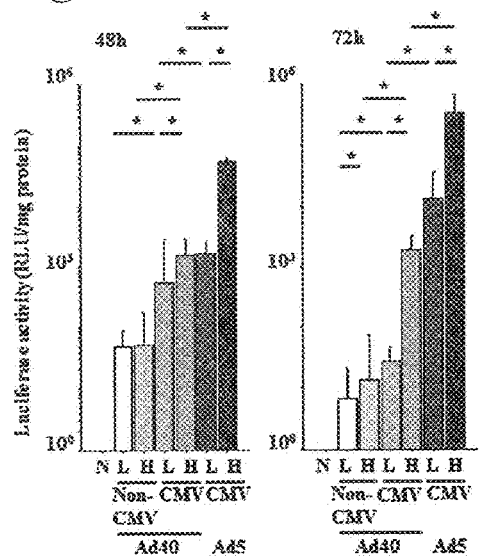
Figure 4D:
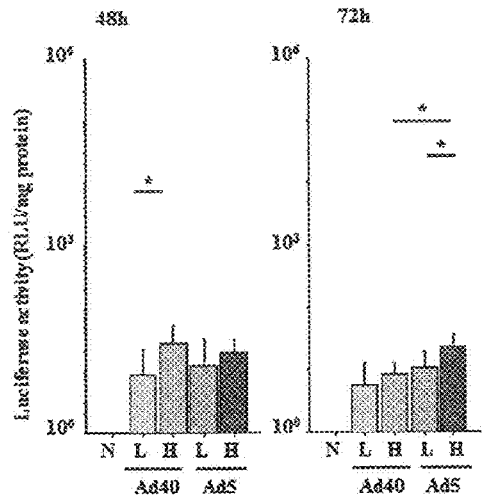
Figure 4E:
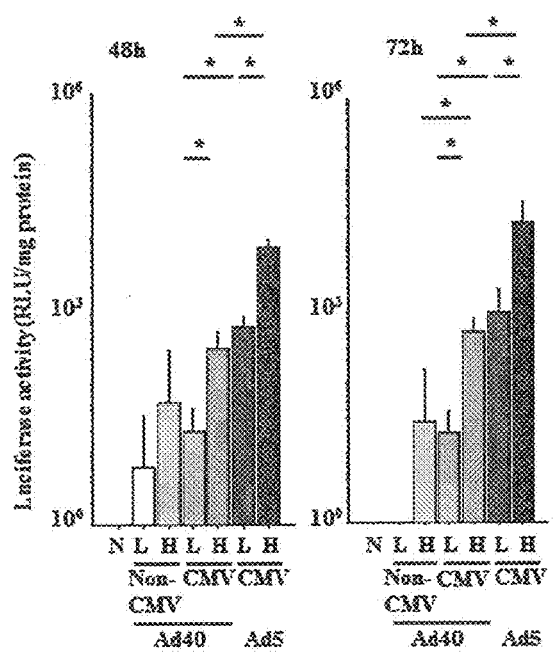
Figure 4F:
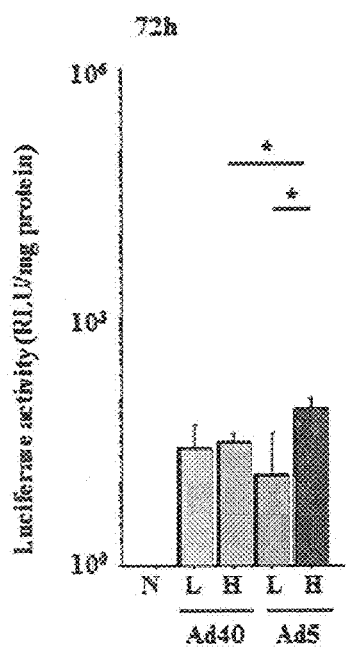

The luciferase activities of Ad40pΔE1-CMV-Luc were significantly higher than those of Ad40pΔE1-Luc in undifferentiated and differentiated CaCo-2 at both 48 and 72 hours (FIG. 4a and FIG. 4c). The luciferase activity in CVL of Ad40pΔE1-CMV-Luc and Ad5-CMV-Luc increased in a dose dependent manner and the luciferase activities of Ad5-CMV-Luc were superior to those of Ad40pΔE1-CMV-Luc in undifferentiated and differentiated CaCo-2, and in vitro M cell model at both 48 and 72 hours (FIG. 4a, FIG. 4c, and FIG. 4e). Pepsin treatment reduced the luciferase activities of both Ad40pΔE1-CMV-Luc-infected cells and Ad5-CMV-Luc-infected cells. However, in both the pepsin-treated and non-treated groups, luciferase activities of Ad5-CMV-Luc were superior to those of Ad40pΔE1-CMV-Luc in undifferentiated CaCo-2 cells at both 48 and 72 hours, and were superior to differentiated CaCo-2 cells and in vitro M cell model at 72 hours (FIG. 4b, FIG. 4d, and FIG. 4f).

Biodistribution of Luciferase Expression Vectors in C57BL/6 Mice.

Figure 5A:
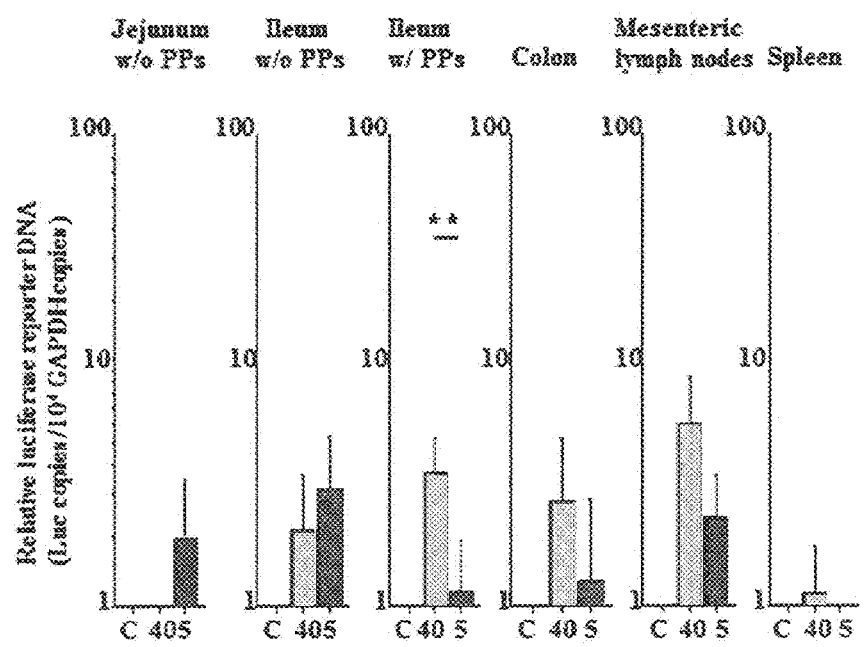
Figure 5B:
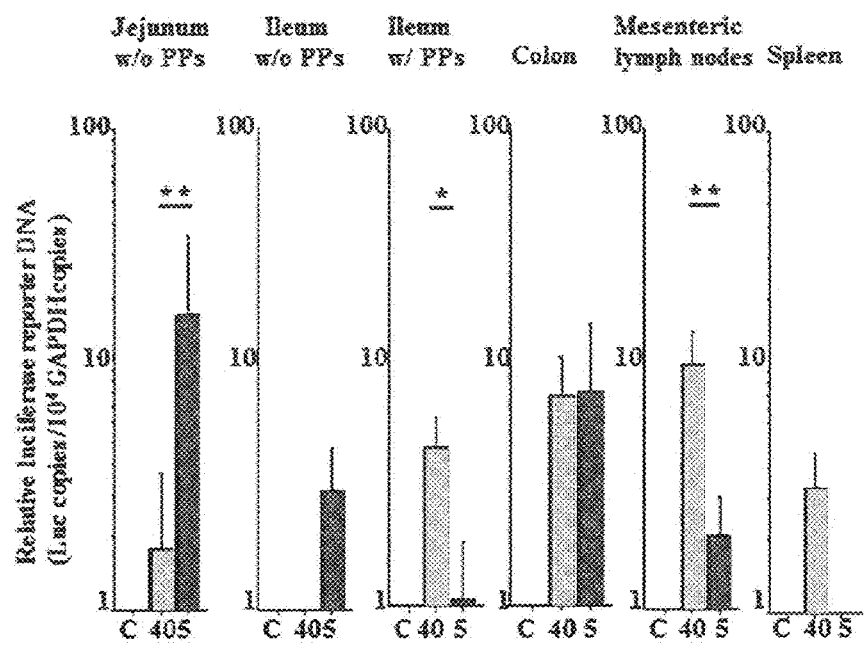

FIG. 5 shows in vivo biodistribution evaluated by the relative copy numbers of luciferase reporter DNA (expressed as luciferase reporter DNA per murine GAPDH DNA) at 48 hours after oral (FIG. 5a) or intraduodenal (FIG. 5b) administration.

After either oral or intraduodenal administration, the relative luciferase copy number of Ad40pΔE1-CMV-Luc was significantly higher than those of Ad5-CMV-Luc in the ileum with PPs. Also, the luciferase reporter DNA of Ad40pΔE1-CMV-Luc, but not that of Ad5-CMV-Luc, was detectable in the spleen (FIG. 5a and FIG. 5b).

After oral administration, luciferase reporter DNA of neither Ad40pΔE1-CMV-Luc nor Ad5-CMV-Luc was detectable in the duodenum. The luciferase reporter DNA of Ad5-

CMV-Luc was detectable in the jejunum without PPs (FIG. 5a). There was no statistically significant difference in luciferase copy number between Ad40pΔE1-CMV-Luc and Ad5-CMV-Luc in the ileum without PPs, in the colon, or in the mesenteric lymph nodes.

After intraduodenal administration (FIG. 5b), the luciferase copy numbers of Ad40pΔE1-CMV-Luc were significantly higher than those of Ad5-CMV-Luc in the mesenteric lymph nodes. The luciferase copy numbers of Ad5-CMV-Luc were significantly higher than those of Ad40pΔE1-CMV-Luc in the jejunum without PPs, the luciferase reporter DNA of Ad5-CMV-Luc was detectable in the ileum without PPs, and there was no statistically significant difference of luciferase copy numbers between Ad40pΔE1-CMV-Luc and Ad5-CMV-Luc in the colon.

Figure 6C:
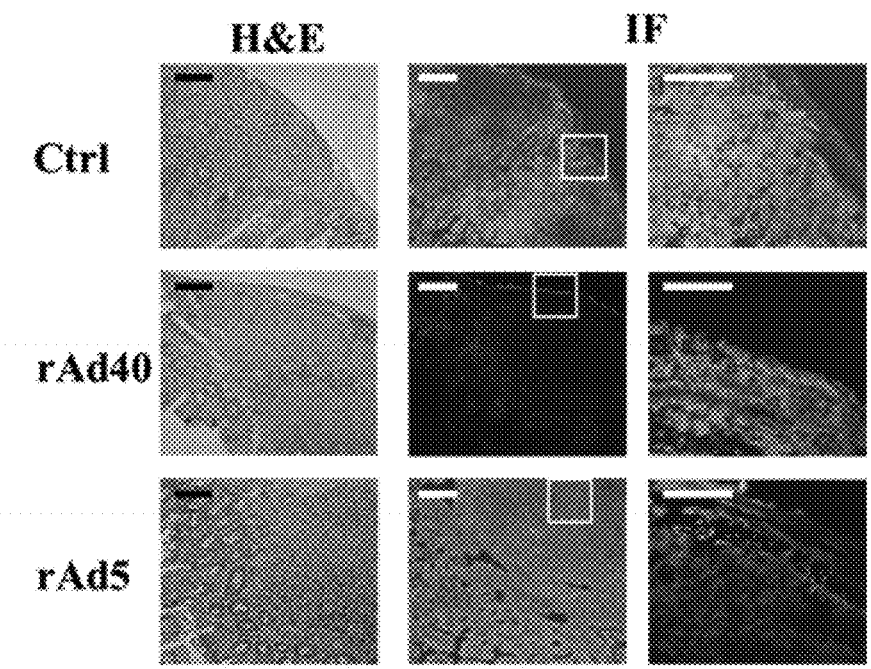

FIG. 6 shows in vivo biodistribution evaluated by the luciferase immunohistochemistry at 48 hours after oral or intraduodenal administration. After either oral or intraduodenal administration of Ad40pΔE1-CMV-Luc, strong luciferase expression was localized in the ileum around PPs' domes. However, scarce luciferase expression was found in the jejunum and ileum after either oral or intraduodenal administration of Ad5-CMV-Luc. Luciferase expression was not detected in the ileal PPs' domes after either the oral or intraduodenal administration of Ad40pΔE1-CMV-Luc or Ad5-CMV-Luc. Further luciferase expression was not detected in the mesenteric lymph nodes or in the spleen after intraduodenal administration of Ad40pΔE1-CMV-Luc and Ad5-CMV-Luc. FIG. 6c shows in vivo biodistribution analysis by luciferase immunofluorescence at 48 h after intraduodenal administration with rAd40-Luc detected consistent luciferase expression in the ileum containing PPs (mainly in CD11c negative cells), while expression was found in the jejunum after intraduodenal administration with rAd5-Luc (Table 2). Luciferase expression was not detected in the MLNs, spleen, and liver after intraduodenal administration with rAd40-Luc and rAd5-Luc. These data suggest that PPs may be the main entry site for rAd40 and transgenes expressed by rAd40 can stimulate both intestinal and systemic immunity. In contrast, the jejunal epithelial cells may be the main entry site for rAd5 and transgenes expressed by rAd5 can stimulate the liver.

TABLE 2

| In vivo luciferase fluorescence | | | |
|---|---|---|---|
| | Control | rAd40-Luc | rAd5-Luc |
| Jejunum w/o PP | 0/9[a] | 2/9 | 9/9 |
| Ileum w/o PP | 0/3 | 1/3 | 1/3 |
| Ileum w/ PPs | 0/3 | 3/3 | 0/3 |
| Colon | 0/3 | 2/3 | 2/3 |
| MLNs | 0/9 | 0/9 | 0/9 |
| Spleen | 0/9 | 0/9 | 0/9 |
| Liver | 0/9 | 0/9 | 0/9 |

[a]Three different samples from three different sites in each mice are shown.
rAd40-Luc, rAd40pΔE1-CMV-Luc;
rAd5-Luc, rAd5-CMV-Luc;
PPs, Peyer's patches;
MLNs, mesenteric lymph nodes;
w/o, without;
w/, with (containing).

These studies indicate that Ad40-based vectors specifically target intestinal M cell and PPs. In addition, neither Ad40-based vectors nor Ad5-based vectors appear stable in the presence of pepsin treatment in vitro. Also, intraduodenal administration appears more effective than oral administration for inducing an intestinal mucosal immune response and/or a systemic immune response, perhaps due the effects of murine gastric fluid.

The amplification of an Ad40 E1A and E1b19K deletion mutant was stable in 911 cells, although that of wild type Ad40 was stable only in Ad5 E4orf6-inducible Ad5 E1-expressing human embryonic kidney (2V6.11) cells. This observation may be explained by low transcriptional activity of the Ad40 E1B promoter and by the ability of Ad E1b19K to inhibit cell lysis. The 911 cells express the Ad5 E1B promoter, whose activity is approximately 100-fold higher than that of Ad40 E1B promoter. In addition, Ad2 E1b19K is a Bcl-2 homolog that blocks apoptosis induction. The Ad2 E1b19K deletion mutant showed significantly enhanced viral spread relative to wild type Ad2 in vitro. The novel partially E1-deleted Ad40-based vectors may exhibit increased transcriptional activity compared to the wild type Ad40. Without wishing to be bound by any particular theory, the increased transcriptional activity may result from expression from the Ad5 E1B promoter endogenous in 911 and/or the presence of an Ad40 E1b19K deletion.

The in vitro pepsin treatment reduced luciferase activities of Ad40pΔE1-CMV-Luc. Additionally, the luciferase copy numbers of Ad40pΔE1-CMV-Luc after intraduodenal administration were higher than those after oral administration in each of the mesenteric lymph nodes and the spleen. Thus, intraduodenal Ad40-based vector administration might induce better systemic stimulation compared to oral administration of the vector.

Naturally, Ad40 often causes diarrhea, mainly in children under two years of age, where the gastric pH is higher than that of adult. The higher pH of gastric acid in infant patients may explain why Ad40 causes diarrhea more frequently in young children than in adults. These data indicate that Ad40-based vectors can be susceptible to protease degradation in a highly acidic environment (e.g., pH≤2). Thus, oral administration of an Ad40-based vector may involve using enteric-coated tablets to help protect the functionality of the vector.

Ad40-based vector showed better binding to in vitro M cell models and higher luciferase reporter DNA copy numbers in the murine ileum with PPs compared to the Ad5-based vector. Ad40, like Ad41, lacks the RGD motif in the penton base. The natural tropism of Ad5 binding to the epithelial cells in the GI tract involves binding to the coxsackievirus and Ad receptor (CAR) and to integrin by an RGD motif in the penton base. These data indicate that Ad5-based vectors may be able to bind to various kinds of epithelial cells in the GI tract, which also may explain why Ad5-based vectors did not have the specificity to intestinal M cells and PPs after oral and intraduodenal administration.

This study compares the biodistribution of Ad40-based and Ad5-based vectors in mice. M cells and PPs are the likely entry sites of an Ad40-based vector, but not those of Ad5-based vector, after oral administration or intraduodenal administration. This result suggests that an Ad40-based vector may be superior to an Ad5-based vector for oral vaccination and/or intraduodenal administration.

Thus, in one aspect, the invention provides a genetically modified polynucleotide that includes an Ad40-based vector comprising a genetic modification that decreases expression of an E1 coding region; and a heterologous polynucleotide.

The genetic modification can be any type of modification effective to decrease expression of an E1 coding region. In some embodiments, for example, the genetic modification that decreases expression of an E1 coding region can include a deletion of at least a portion of the E1 coding region or of at least a portion of a regulatory region that, when present, is required for expression of the E1 coding region. Decreased E1 expression permits the genetically modified polynucleotide to be amplified in a wider range of cell types than existing adenovirus-based vectors that require specific cell types for large-scale amplification. An exemplary genetic modification of the E1 coding region that decreases E1 expression can include, for example, a full deletion of the E1A coding region. Another exemplary genetic modification that decreases E1 gene expression can include an E1b19K deletion—a deletion of 1251 bp from 442 to 1692 of Gen-Bank accession no. L19443.

The genetically modified polynucleotide further includes a heterologous polynucleotide. In certain embodiments, the genetically modified polynucleotide can be constructed to deliver a therapeutic or prophylactic polynucleotide sequence. The prophylactic and/or therapeutic polynucleotide can be any polynucleotide sequence that can serve as a component of treatment for a medical condition. Common types of prophylactic and/or therapeutic polypeptides include polypeptides that encode a polypeptide that is effective for treating a condition. Such polypeptides can include, for example, certain antigens that can induce an immune response against an infection, antigens that can induce immune tolerance of the antigen, or certain cytokines that can shift the immune function of the subject to some degree to either (a) assist an immune response against an infection, or (b) decrease inflammation associate with, for example, an inflammatory condition. In other cases, the prophylactic and/or therapeutic polynucleotide can be a polynucleotide that encodes an interfering polynucleotide such as, for example, an interfering RNA (e.g., an siRNA or an miRNA). In these embodiments, the interfering polynucleotide may be selected to interfere with—i.e., reduce to any degree—expression of a polypeptide that is associated with the medical condition for which treatment is indicated.

Table 3 lists exemplary types of conditions and exemplary prophylactic and/or therapeutic polynucleotides that may be incorporated into an Ad40-based genetically modified polynucleotide.

TABLE 3

| Field | Target Disease Category | Disease/Pathogen | Prophylactic/ Therapeutic polynucleotide |
|---|---|---|---|
| Cancers | GI cancer | pancreatic cancer | mesothelin |
| | | | Muc-1 |
| | | colon cancer | carcinoembryonine antigen (CEA) |
| | | | Muc-1 |
| | | gastric cancer | CEA |
| | lung cancer | lung cancer | CEA |
| | | mesothelioma | mesothelin |
| | pediatric cancer | Wilms' tumor | midkine |
| | | neuroblastoma | midkine |
| Infectious Diseases | Bacteria | *Yersinia pestis* | *Y. pestis* antigens F1 |
| | | | *Y. pestis* antigen V |
| | | *Bacillus anthracis* | PA antigen |
| | Virus | HIV/AIDS | gp120 |
| | | | gag/pol/nef |
| | | | gp160 |
| | | | multiple envelope antigens |
| | | HPV | E6 |
| | | | E7 |
| | | | L2 |
| | Parasite | malaria | merozoite surface protein 1 (MSP-1) |

TABLE 3-continued

| Field | Target Disease Category | Disease/Pathogen | Prophylactic/ Therapeutic polynucleotide |
|---|---|---|---|
| | | | apical membrane antigen-1 (AMA-1) |
| Inflammatory diseases | inflammatory bowel diseases | Crohn's disease | TGF-β1 |
| | | | IL-10 |
| | | ulcerative colitis | TGF-β1 |
| | | | IL-10 |
| | Celiac Disease | | prolamins |
| | Type I Diabetes mellitus | | |
| | Rheumatoid Arthritis | | |
| | Allergy | | Any allergen |

We therefore evaluated the Ad40 vector for use as a vaccine vector for treating either inflammatory disease (e.g., allergy) or for treating cancers (e.g., pancreatic cancer Immune Responses of Ad Vectors Expressing Ovalbumin In Vivo.

Ova was used as a model antigen to test the Ad40 vector as a vehicle for inducing immune tolerance of an antigen encoded by the vector. Such a vaccine may be effective in the treatment of inflammatory diseases such as, for example, allergy (including allergy to foods, hay fever, etc.) or autoimmune diseases such as, for example, celiac disease, inflammatory bowel diseases, type 1 diabetes mellitus, and rheumatoid arthritis.

The number of Ova-specific cytotoxic T lymphocytes (CTLs, Pentamer H-2K$^b$-SIINFEKL+CD8a+CD19−) increased in the spleen and liver at 14 days after intraduodenal administration with rAd40pΔE1-CMV-Ova (rAd40-Ova) or rAd5-CMV-Ova (rAd5-Ova) into B6 mice (FIG. 8a), but returned to baseline levels at 42 days post intraduodenal administration (FIG. 8b). The numbers of interferon-γ (IFN-γ)-secreting CD8+ T cells (IFN-γ+CD3e+CD8a+) stimulated by Ova-peptide (SIINFEKL; SEQ ID NO:23) or Pan02-Ova cell lysates were increased in the spleen and liver only by rAd40-Ova at 14 days after intraduodenal administration (FIG. 8c), but not at day 42. Thus, our data indicate that systemic tolerance may be induced at 14 days after intraduodenal administration with rAd5 and 42 days with rAd40. The numbers of Foxp3+ cells in MLNs were increased by intraduodenal administration with rAd compared to the control at day 14 (FIG. 8d). The numbers of Foxp3+ cells in MLNs induced by rAd40-Ova were the highest, while those induced by rAd5-Ova were significantly lower. The numbers of regulatory T cells (Tregs, CD4+CD25+Foxp3+) in MLNs at 42 days post intraduodenal administration maintained high showing the same tendencies as those of Foxp3+ cells at day 14 (FIG. 8e). These results show that rAd40-Ova can stimulate the intestinal mucosal immunity to a greater extent than rAd5-Ova.

Ova-specific IgG1 was detectable in serum 14 days after intraduodenal administration of rAd40-Ova and rAd5-Ova (FIG. 8f). The peak of IgG1 activity was 14 days in rAd5-Ova and 21 days in rAd40-Ova (FIG. 8g). IgG1 activity units in rAd40-Ova were significantly higher than those in rAd5-Ova at 21 days, 28 days, and 35 days post intraduodenal administration. Neither serum IgG2a, serum IgE, nor fecal IgA was detectable between days 0 and 42. While rAd40 and rAd5 can induce systemic immunity along a Th2-dependent pathway, rAd40 stimulated a more robust systemic immune response with a later peak than rAd5.

Inhibition of Ovalbumin-Induced Delayed-Type Hypersensitivity Response.

Figure 9A:
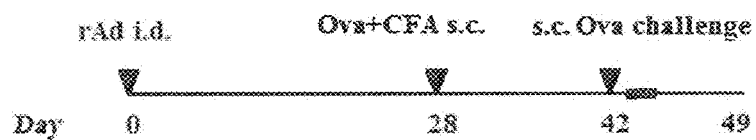
Figure 9B:
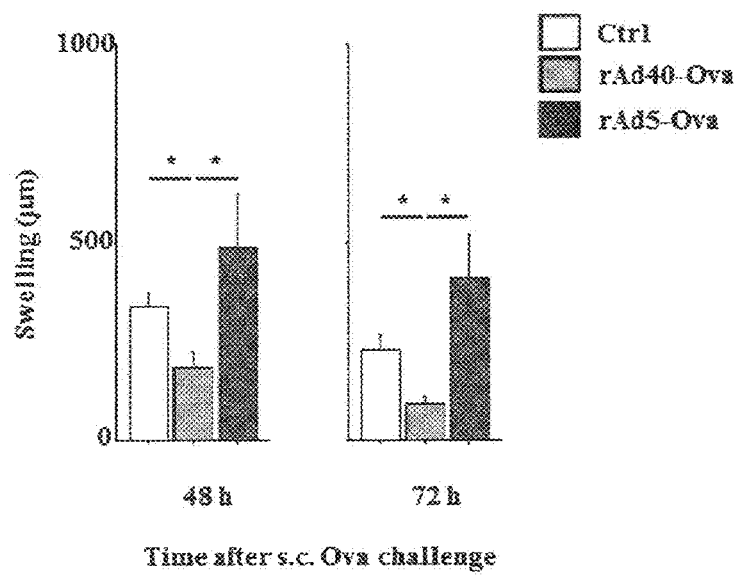
Figure 9C:
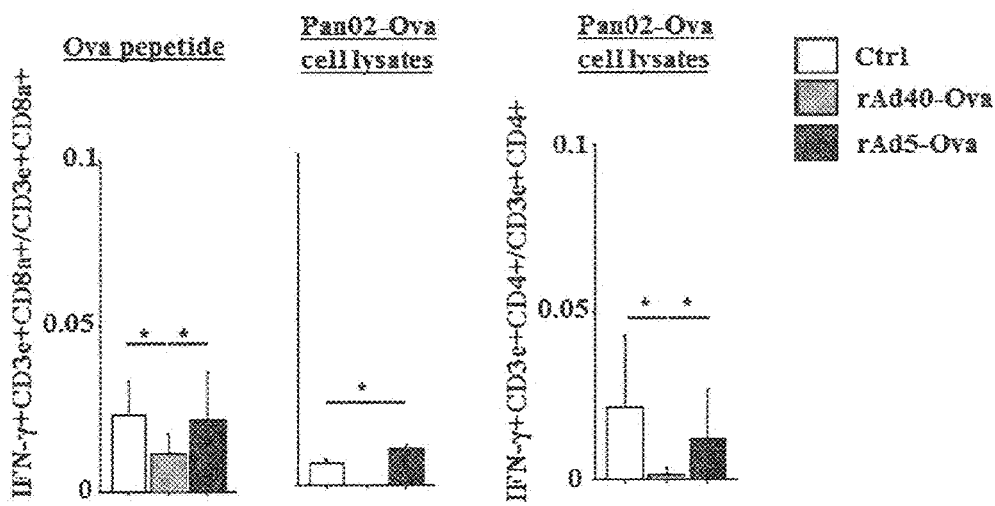

To evaluate whether it was possible to induce systemic tolerance after intraduodenal administration with Ova expressing rAd, delayed-type hypersensitivity reactions were tested (FIG. 9a). Both 48 hours and 72 hours after subcutaneous Ova challenge, delayed-type hypersensitivity reactions were reduced only by rAd40-Ova (FIG. 9b). The ratios of splenic Ova-specific IFN-γ-secreting CD8+ T cells to CD8+ T cells, IFN-γ-secreting CD4+ T (IFN-γ+CD3e+CD4+) cells to CD4+ T cells, IFN-γ-secreting NKT cells (IFN-γ+NK1.1+CD3e+) to NKT cells, and IFN-γ-secreting NK cells (IFN-γ+NK1.1+CD3e−) to NK cells were decreased by rAd40-Ova at 7 days after subcutaneous challenge (FIG. 9c). These data suggested that Ova-specific activation of lymphocytes in the systemic immunity was suppressed by rAd40-Ova.

Inhibition of Ovalbumin-Induced Diarrhea and Systemic Anaphylaxis.

Figure 10A:
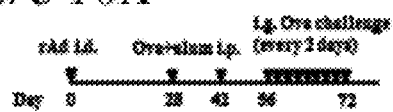
Figure 10B:
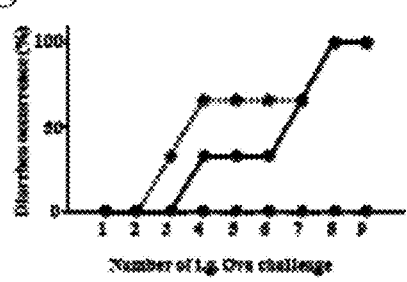
Figure 10C:
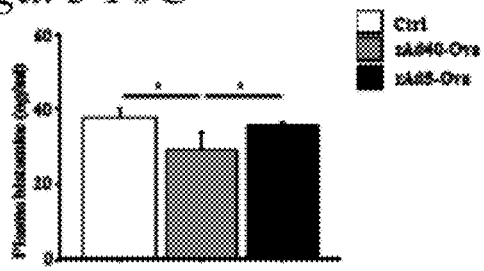
Figure 10D:
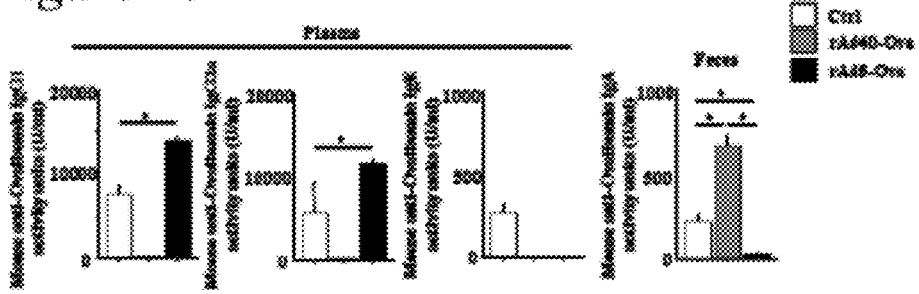

To examine the inhibition of Ova-induced diarrhea in rAd40-Ova-pretreated BALB/c mice, we used a food allergy model (FIG. 10a). We observed the percentage of diarrhea occurrence following each of the nine intragastric Ova challenges (FIG. 10b). After eight consecutive intragastric Ova challenges, profuse liquid stool was observed in all control mice, while small amounts of liquid stool and frequent bowel movements were observed in all rAd5-Ova-pretreated mice. No diarrhea was observed in any of the rAd40-Ova-pretreated mice. One hour following the last intragastric challenge, plasma histamine levels (FIG. 10c) and the activities of plasma Ova-specific IgG1 and IgG2a (FIG. 10d) were significantly suppressed in rAd40-Ova-pretreated mice. However, the activities of fecal Ova-specific IgA were significantly increased in rAd40-Ova-pretreated mice compared to control and rAd5-Ova-pretreated mice, corresponding with the inhibition of Ova-induced diarrhea occurrence with rAd40-Ova-pretreated mice. Plasma Ova-specific IgE, a mediator for type I hypersensitivity, was mobilized only in control mice.

Figure 11A:
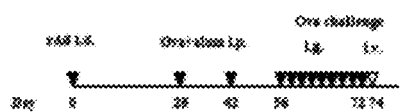
Figure 11B:
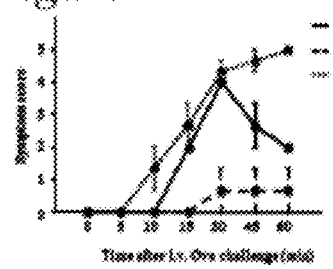
Figure 11C:
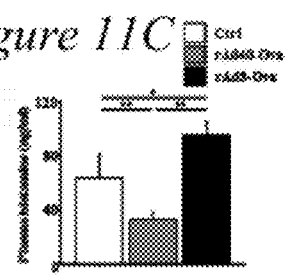

The effect on severe systemic allergic reaction was analyzed in an anaphylaxis model. Systemic anaphylaxis was measured by symptom score (Roy et al., 1999 Nat. Med. 5, 387-391) up to 60 minutes after an intravenous Ova challenge to Ova-induced diarrhea mice (48 hours after final intragastric challenge following allergic diarrhea models, FIG. 11a, b). All control mice developed behavioral symptoms of "no activity" (score 4) at 30 minutes after intravenous challenge, but recovered to a score 2 (less severe) within 60 minutes. All rAd5-Ova-pretreated mice progressed to a score 5 (death) due to anaphylactic shock within 60 minutes. In contrast, fewer and less-severe (score 0-2) responses were seen in rAd40-Ova-pretreated mice after intravenous challenge. After nine intragastric challenges and 15 minutes after intravenous challenge, plasma histamine levels in rAd40-Ova-pretreated mice were similar to levels after one hour following the last intragastric challenge (before intravenous challenge), but plasma histamine levels in control and rAd5-Ova-pretreated mice increased (FIG. 11c). Moreover, plasma histamine levels in rAd5-Ova-pretreated mice were higher than in control mice (FIG. 11c).

Figure 11D:
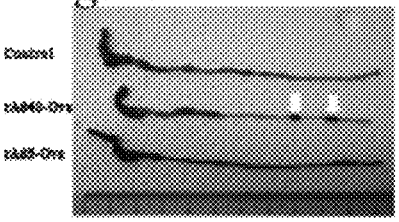

These results indicate that rAd40-Ova can inhibit systemic anaphylactic reactions, while rAd5-Ova failed to ameliorate allergic reactions compared to reactions in control mice. After nine intragastric challenges and 60 minutes after intravenous challenge, diarrhea was noted by macroscopic observation of the colon and cecum, illustrated by the liquid stool observed in all control and rAd5-Ova-pretreated mice, and contrasted with the solid stool pellets found in the distal colon of all rAd40-Ova-pretreated mice (FIG. 11d). The rAd5-Ova-pretreated mice exhibited markedly red colons after anaphylactic shock, and bloody diarrhea was observed in the jejunum.

Figure 11E:
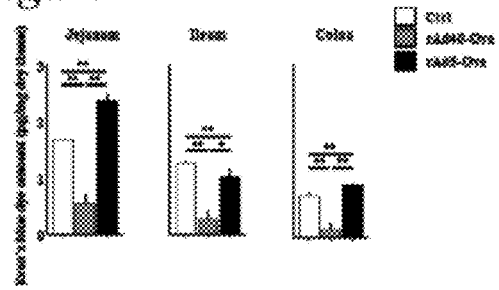

To evaluate vascular permeability, Evan's blue extravasation in the tissues was measured. Evan's blue concentrations throughout the intestinal system—i.e., jejunum, ileum, and colon—of rAd40-Ova-pretreated mice were significantly lower than in those of control and rAd5-Ova-pretreated mice (FIG. 11e). The jejunum of rAd5-Ova-pretreated mice showed more Evan's blue extravasation than those of control mice, consistent with the observation of bloody diarrhea and the detection of higher luciferase copy numbers or constant luciferase expression of rAd5-Luc in the in vivo biodistribution assay. Greater extravasation was observed in the colon of rAd5-Ova-pretreated mice compared to control mice, corresponding with remarkable redness.

Figure 11F:
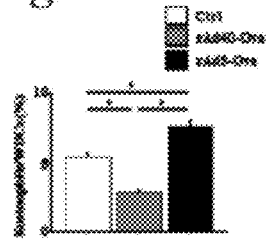

To evaluate the systemic responses, numbers of bone marrow eosinophils were measured at 60 minutes after intravenous challenge (FIG. 11f). The number of eosinophils was lower in rAd40-Ova-pretreated mice, reflecting plasma histamine levels at 15 minutes. We show that rAd40 induces a different type of oral tolerance to the model antigen Ova compared with rAd5, which may be explained by differences between main entry sites of the two vectors—i.e., PPs for rAd40 and jejunal epithelial cells for rAd5. Although rAd40 expressed lower levels of protein in vitro than rAd5, the numbers of Tregs in MLNs at 14 days and 42 days after intraduodenal administration with rAd40-Ova were higher than those induced by rAd5-Ova. At 14 days post intraduodenal administration, rAd40-Ova was able to induce functional Ova-specific CTLs in both spleen and liver. The Ova-specific CTLs found in spleen and liver at 14 days post intraduodenal administration were not detected at 42 days after intraduodenal administration. These observations illustrate that intraduodenal administration with rAd40 can induce intestinal and/or portal venous tolerance mediated by gut-homing of intestinal immune cells.

The rAd40-Ova induced mucosal and systemic tolerance. To our surprise, delayed-type hypersensitivity to Ova was markedly reduced by rAd40-Ova pretreatment. Moreover, rAd40-Ova completely suppressed diarrhea occurrence and systemic anaphylaxis—corresponding with the activities of Ova-specific IgG1, IgG2a, and IgE. rAd40-Ova also suppressed histamine levels, intestinal vascular permeability, and the number of bone marrow eosinophils. Only control mice showed the induction of Ova-specific IgE, a mediator for type I hypersensitivity. Although symptoms of systemic anaphylaxis in all control mice recovered within 60 minutes after intravenous Ova challenge, all rAd5-Ova treated mice died. These results indicate that rAd5-Ova can worsen delayed-type hypersensitivity, type IV hypersensitivity mediated by T cells, and the cross-reaction of type I hypersensitivity and IV hypersensitivity experienced in the rAd5-Ova pretreated mice induced lethal responses. However, rAd40-Ova treatment of mice can inhibit both type I and IV hypersensitivity.

In this study, we demonstrate that our Ad40-based vector can be effective for treating inflammatory responses against a model antigen. The Ad40-based vector proved effective in inhibiting both allergen-specific IgG antibodies and allergen-specific IgE antibodies. An Ad40-based vector may, therefore, increase the efficacy of allergy treatment. The use of a single vaccine can increase patient compliance and clinical safety. Our methods provide availability of clinically-effective recombinant allergens against anaphylaxis, allowing independence from natural raw allergen-containing materials.

We next turned to evaluate whether the Ad40-based vector could deliver an anti-cancer therapeutic. Pancreatic cancer is a leading cause of cancer death for both men and women in the United States due, at least in part, because it is notoriously difficult to detect early and/or resect the tumor before it can metastasize. Mesothelin is a 40-kDa glycosylphosphatidylinositol (GPI)-linked cell surface glycoprotein derived from a 71-kDa precursor that is evaluated as an immunotherapeutic target in mesothelin overexpressing cancers, including pancreatic cancer. Mesothelin is overexpressed in pancreatic ductal adenocarcinoma, while it is not expressed in normal tissue and chronic pancreatitis. Mesothelin can promote anchorage-independent growth and can prevent anoikis via the Erk signaling pathway in human breast cancer. In human pancreatic cancer, mesothelin can induce cell proliferation via the Stat3 signaling pathway. Additionally, circulating mesothelin can be a useful marker for pancreatic cancer. The Pan02 (Corbett et al., 1984 Cancer Res 44(2):717-726) cell line is derived from a mouse pancreatic ductal adenocarcinoma and is often used for mouse pancreatic cancer models.

Antitumor Immune Responses by Ovalbumin Expression Vectors.

To evaluate antitumor immune responses against Ova-expressing tumor, we used a subcutaneous mouse model with Pan02-Ova, which expresses Ova, or Pan02-LuciGFP, which lack Ova. At 14 days after intravenous vaccination with either PBS, rAd40-Ova, or rAd5-Ova, either Pan02-Ova or Pan02-LuciGFP cells ($5 \times 10^5$ cells/mouse) were inoculated subcutaneously into B6 mice, then observed for 30 days after tumor challenge. As early as six days after tumor challenge, the rAd40-Ova-vaccinated mice challenged with Pan02-Ova exhibited statistically significantly smaller tumor volumes compared to mice vaccinated with either PBS or rAd5-Ova (FIG. 12, a and b). Moreover, the number of Ova-specific CTLs present in the spleen of rAd40-Ova-pretreated mice 30 days after tumor challenge was greater to a statistically significant extent than CTLs in the spleens of either PBS-pretreated or rAD5-Ova-pretreated mice (FIG. 12c). Also, the number of IFN-γ-secreting CD8+ T cells stimulated by Ova-peptide and Pan02-Ova lysates in rAd40-Ova-pretreated mice were higher than those in PBS-pretreated and rAd5-Ova-pretreated mice.

Antitumor Immune Responses by Mesothelin Expression Vectors.

Figure 13A:
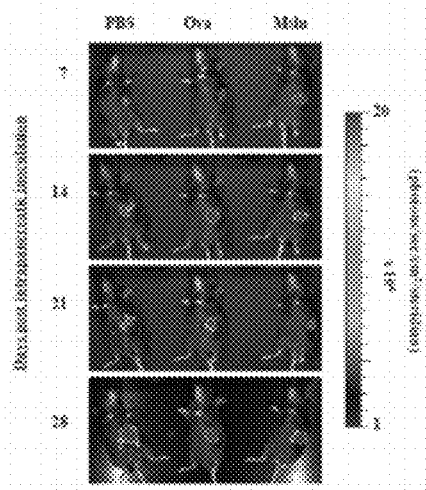

To test the effect of rAd40-Msln on metastasis, an orthotopic pancreatic cancer model with Pan02-LuciGFP was used. Untreated (i.e., PBS-pretreated) orthotopically transplanted Pan02-LuciGFP tumors rapidly produced extensive locoregional and systemic metatstases. Luciferase gene expression from metastasized Pan02-LuciGFP was detected in PBS-pretreated mice in the spleen, periportal and intestinal lymph nodes, and peritoneum (FIG. 13A). At autopsy (day 29 after tumor inoculation), all PBS-preheated and rAd40-Ova-pretreated mice showed metastatic diseases in the spleen, gastrointestinal, and periportal and intestinal lymph nodes. In addition, some PBS-pretreated and rAd40-Ova-pretreated mice exhibited metastases.

Figure 13B:
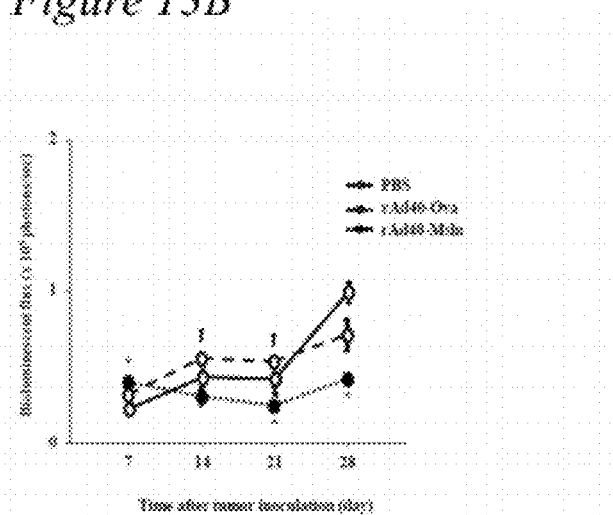
Figure 13C:
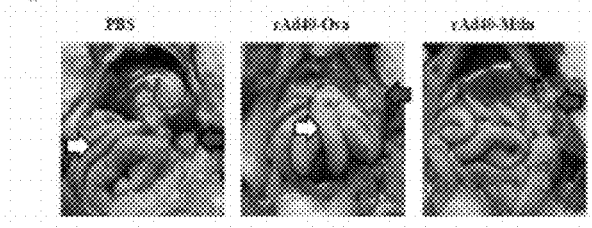

In contrast, no rAd40-Msln-pretreated mice had metastases in the liver or peritoneum. Also, rAd40-Msln-pretreated mice exhibited lower levels of abdominal bioluminescence compared to PBS-pretreated and rAd40-Ova-pretreated mice (FIG. 13B). Thus, only rAd40-Msln suppressed the organ distribution of metastases in the orthotopic Pan02-LuciGFP tumor model. Furthermore, macroscopic intestinal obstruction was found in both PBS-pretreated and rAd40-Ova-pretreated mice, but not in rAd40-Msln-pretreated mice (FIG. 13C).

Figure 13D:
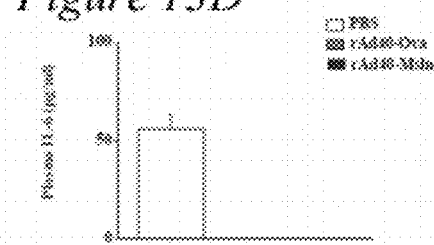

To observe the responses of inflammatory markers in orthotopic models, IL-6 plasma levels were measured (FIG. 13D). Plasma IL-6 was upregulated only in PBS-pretreated mice after orthotopic Pan02-LuciGFP inoculation. Tumors had histologic features consistent with pancreatic carcinoma visualized with hematoxylin and eosin (H&E) staining (FIG. 14). Also, GFP expression in all tumors was evaluated by immunofluorescence. Splenocytes at autopsy yielded higher number of cells in the monocyte-gates at FSC/SSC dot-plots, especially in PBS-pretreated mice (FIGS. 15, A and B). The higher numbers of GFP-expressing splenocytes were detected in the monocyte-gates of PBS-pretreated mice compared to rAd40-pretreated mice (FIGS. 15, C and D). Pretreatment with rAd40-Msln resulted in a reduction in carcinomatosis and metastases to the spleen. Additionally, pretreatment with rAd40-Msln reduced the frequency of metastases to liver, gastrointestinal tract, lymph nodes, and peritoneum compared to pretreatment with eithr PBS or rAd40-Ova.

Figure 16A:
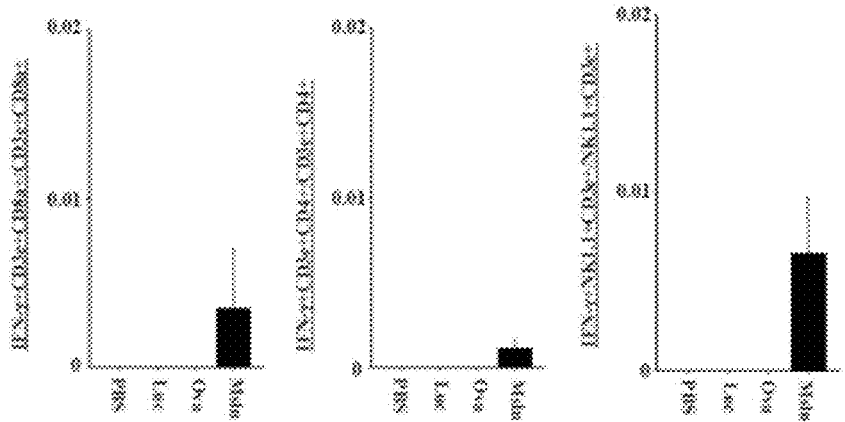
Figure 16B:
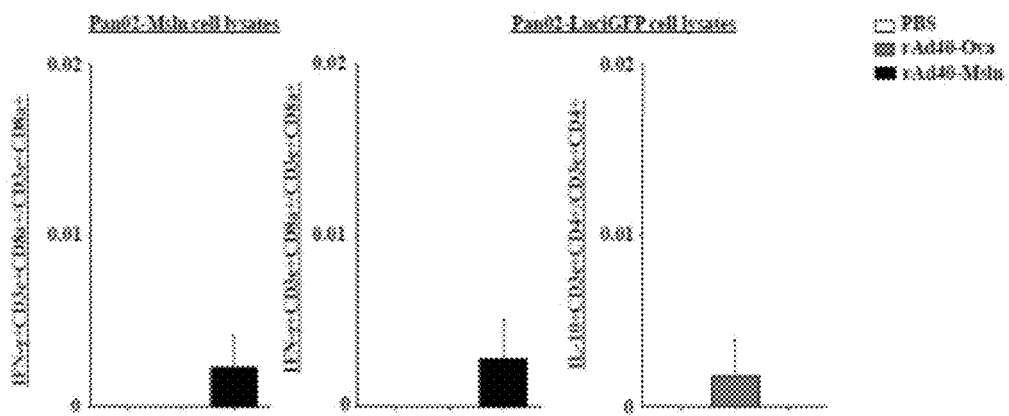

To confirm the modulation of Th1-mediated immune responses with rAd40-Msln, we detected Pan02-Msln-specific IFN-γ-secreting CD8+, CD4+, and NK1.1+ T cells in the spleen at 14 days after intravenous administration of rAd40-Msln (FIG. 16A). In addition, Pan02-Msln-specific IFN-γ-secreting CD8+ T cells were found at day 29 after orthotopically Pan02-LuciGFP inoculation only in rAd40-Msln-pretreated mice (FIG. 16B). To our surprise, Pan02-LuciGFP-specific IFN-γ-secreting CD8+ T cells were observed in rAd40-Msln-pretreated mice. In contrast, Pan02-LuciGFP-specific IL-10 secreting CD4+ T cells were seen in rAd40-Ova-pretreated mice, indicating the systemic tolerance induced by tumor inoculation.

Thus, we show that intravenous rAd40 administration can stimulate systemic antigen-specific immune responses. Furthermore, a single intravenous administration with rAd40 inhibited antigen-specific pancreatic cancer growth and the number of metastases in a mouse model. Intravenously administered rAd40-Ova induced functional Pan02-Ova-specific systemic immunity along a CTL and Th1-dependent pathway. Also, intravenous rAd40-Msln suppressed tumor growth and the number of metastases in a mouse orthotopic pancreatic model.

In contrast, transgenes expressed by rAd5 can stimulate the immune reaction in the liver. Liver antigen-presenting cells can regulate liver tolerance and the induction of peripheral tolerance. As a result, intravenous rAd5-Ova failed to induce either a functional Pan02-Ova-specific CTL response or Pan02-Ova tumor suppression in vivo, consistent with rAd5-Ova inducing liver tolerance.

Our results present intravenous administration of rAd40 as an Ad-based vector system that can provide wider biodistribution, fewer and reduced inflammation responses, less liver toxicity, stable immune responses, and/or effective antitumor activity in mice compared to intravenous administration of a conventional rAd5-based vaccine. Our Ad40-based vector system can be used to address problems with observed using existing therapies for metastatic cancers.

Thus, in another aspect, the invention provides pharmaceutical compositions that include a genetically modified polynucleotide and/or Ad40-based viral vector as described above. Such compositions can include a pharmaceutical acceptable carrier. "Pharmaceutically acceptable" refers to a diluent, carrier, excipient, salt, etc., that is compatible with the other ingredients of the composition, and not deleterious to one to whom the composition is administered. A pharmaceutical composition may be formulated in a variety of forms adapted to the chosen route of administration, including routes selected for delivery of the genetically modified polynucleotide or Ad40-based viral vecotr to tissues of the GI tract. Thus, a pharmaceutical composition can be administered via known routes including, for example, orally, intraduodenally, and topically to, for example, a mucosal surface (e.g., intravaginally or rectally). A pharmaceutical composition designed for oral administration may further include an enteric coating to protect the pharmaceutical composition from the acidic environment of the stomach.

In another aspect, the invention provides a method of treating a medical condition. Generally, the method includes administering a pharmaceutical composition as described above to a subject identified as having, or is at risk of having, a medical condition that is treatable by a vector harboring a heterologous prophylactic and/or therapeutic polynucleotide described herein. Exemplary conditions treatable using the methods described herein—and exemplary prophylactic and/or therapeutic heterologous polynucleotides for practicing such methods—are listed in Table 3.

Treating a condition can be prophylactic or, alternatively, can be initiated after the subject exhibits one or more symptoms or clinical signs of the condition. Treatment that is prophylactic—e.g., initiated before a subject manifests a symptom or clinical sign of the condition such as, for example, prior to exposure to an allergen, prior to development of a tumor, prior to infection, or while an infection remains subclinical—is referred to herein as treatment of a subject that is "at risk" of having the condition. As used herein, the term "at risk" refers to a subject that may or may not actually possess the described risk. Thus, for example, a subject "at risk" of infectious condition may be a subject present in an area where other individuals have been identified as having the infectious condition and/or is likely to be exposed to the infectious agent even if the subject has not yet manifested any detectable indication of infection by the microbe and regardless of whether the animal may harbor a subclinical amount of the microbe. As another example, a subject "at risk" of a non-infectious condition is a subject possessing one or more risk factors associated with the condition such as, for example, genetic predisposition, ancestry, age, sex, geographical location, lifestyle, or medical history.

Accordingly, a pharmaceutical composition can be administered before, during, or after the subject first exhibits a symptom or clinical sign of the condition or, in the case of infectious conditions, before, during, or after the subject first comes in contact with the infectious agent. Treatment initiated before the subject first exhibits a symptom or clinical sign associated with the condition may result in decreasing the likelihood, extent, and/or severity of symptoms and/or clinical signs of the condition compared to an animal to which the composition is not administered. Treatment initiated after the subject first exhibits a symptom or clinical sign associated with the condition may result in decreasing the severity of symptoms and/or clinical signs of the condition, completely resolving the condition, and/or decreasing the likelihood of experiencing clinical evidence of the condition compared to an animal to which the composition is not administered.

The method includes administering an effective amount of the composition to a subject having, or at risk of having, a particular condition. In this aspect of the invention, an "effective amount" is an amount effective to reduce, limit progression, ameliorate, or resolve, to any extent, the symptoms or clinical signs related to the condition. In some cases, an effective amount can include a dose of from about $10^8$ viral particles to about $10^{14}$ viral particles, although the methods described herein can be practiced by administering to a subject a dose of Ad40-based vector particles that falls outside of this range. A dose can include, for example, a minimum of at least $10^9$ viral particles, at least $5 \times 10^9$ viral particles, at least $10^{10}$ viral particles, at least $2 \times 10^{10}$ viral particles, at least $3 \times 10^{10}$ viral particles, at least $4 \times 10^{10}$ viral particles, at least $5 \times 10^{10}$ viral particles, at least $6 \times 10^{10}$ viral particles, at least $7 \times 10^{10}$ viral particles, at least $8 \times 10^{10}$ viral particles, at least $9 \times 10^{10}$ viral particles, at least $10^{11}$ viral particles, at least $2 \times 10^{11}$ viral particles, at least $3 \times 10^{11}$ viral particles, at least $4 \times 10^{11}$ viral particles, at least $5 \times 10^{11}$ viral particles, at least $10^{12}$ viral particles, or at least $10^{13}$ viral particles. A dose can include a maximum of no more than $10^{14}$ viral particles such as, for example, no more than $10^{13}$ viral particles, no more than $10^{12}$ viral particles, no more than $5 \times 10^{11}$ viral particles, no more than $4 \times 10^{11}$ viral particles, no more than $3 \times 10^{11}$ viral particles, no more than $2 \times 10^{11}$ viral particles, no more than $10^{11}$ viral particles, no more than $9 \times 10^{10}$ viral particles, no more than $8 \times 10^{10}$ viral particles, no more than $7 \times 10^{10}$ viral particles, no more than $6 \times 10^{10}$ viral particles, no more than $5 \times 10^{10}$ viral particles, no more than $4 \times 10^{10}$ viral particles, no more than $3 \times 10^{10}$ viral particles, no more than $2 \times 10^{10}$ viral particles, no more than $10^{10}$ viral particles, or no more than $5 \times 10^9$ viral particles. A dose also may expressed in terms of a range having endpoints defined by any minimum dose provided herein and any appropriate maximum dose provided herein.

The Ad40-based vector can exhibit the natural tropism for mucosal tissues of the GI tract that is exhibited by wild type Ad40. Therefore, a composition that includes an Ad40-based gene transfer vector may be particularly suited for delivery of prophylactic and/or therapeutic polynucleotides effective for treating intestinal conditions and/or inducing a mucosal immune response. Compositions that include a genetically modified polynucleotide and/or an Ad40-based vector as described herein may be suitable for oral vaccination that targets the intestinal mucosa such as, for example, vaccination that provides prophylactic and/or therapeutic treatment for, for example, colon cancer, ulcerative colitis, AIDS, or Crohn's disease.

In some embodiments, the pharmaceutical composition is administered orally. In other embodiments, the pharmaceutical composition is administered intraduodenally. In some embodiments, the pharmaceutical composition may be administered so that the genetically modified polynucleotide localizes is cells in the Peyer's patch, cells of the colon, cells of mesenteric lymph nodes, or cells of the spleen.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 1:
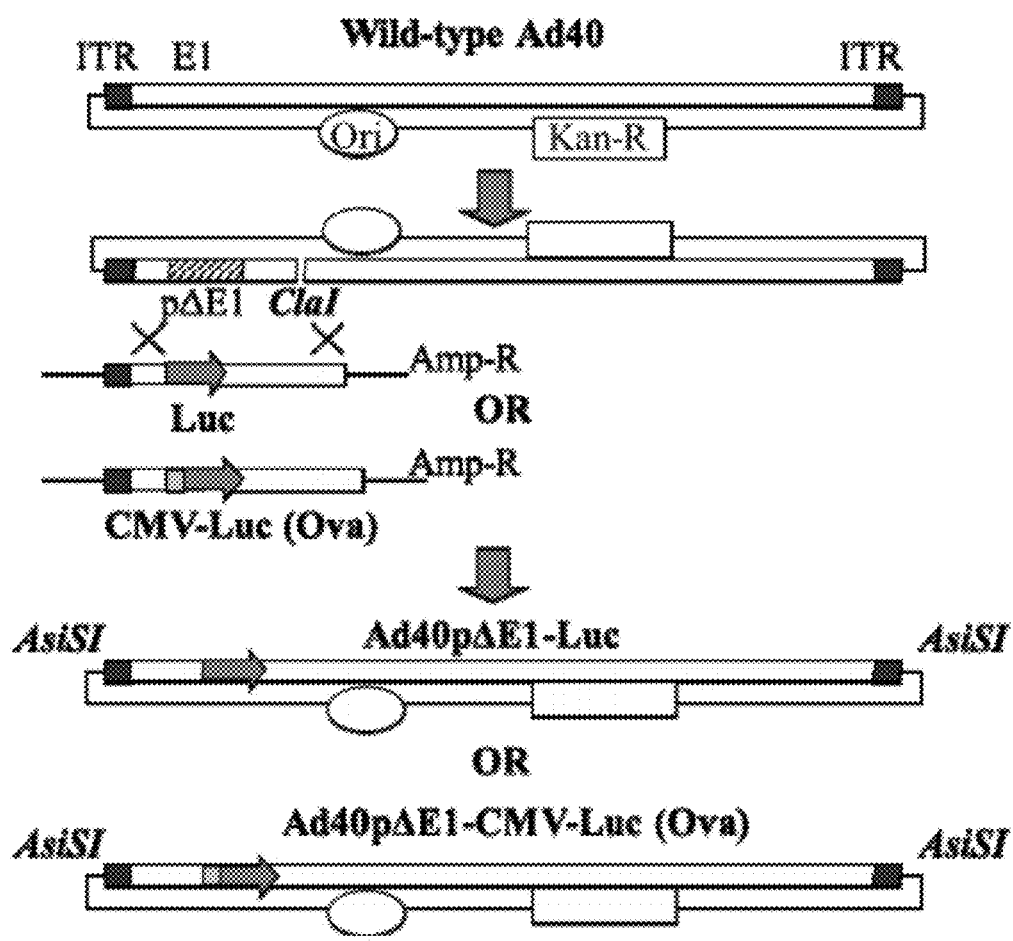
FIG. 1. A schematic representation of the strategy to engineer pAd40pΔE1-Luc, pAd40pΔE1-CMV-Luc, and rAd40-Ova vectors. Though not illustrated, construction of rAd40-Msln was performed similarly, substituting a mesothelin coding region for the Luc or Ova coding region as illustrated. ITR, internal tandem repeat; Ori, origene of $E.\ coli$; Kan-R, kanamycin-resistance gene; Amp-R, ampicillin-resistance gene; CMV, cytomegalovirus promoter; Luc, luciferase reporter; Ova, ovalbumin.

Ad40-based vectors containing a partially deleted E1 region and either a cytomegalovirus (CMV)-promoter driven luciferase reporter gene (Ad40pΔE1-CMV-Luc) or a non-promoter-driven luciferase reporter gene (Ad40pΔE1-Luc) were generated by homologous recombination between a unique ClaI-digested plasmid including wild type Ad40 DNA and a rescue plasmid, which was inserted into homologous regions of Ad40-left and right-ends (left, 441 bp between 1 and 441 of GenBank accession no. L19443; right, 2809 bp between 1693 and 4501) and non-promoter- or CMV-promoter-driven firefly luciferase reporter gene in E. coli (FIG. 1).

Vectors were generated from plasmid DNA by transfection of Ad5 E1-expressing human retinoblastic (911) cells after linearization with AsiS1. At seven days after transfection, the 911 cells were subjected to three freeze-thaw cycles. A series of 1:3 dilution of the resulting crude viral liquids (CVLs), which were prepared by three freeze-thaw cycles and centrifugation (3000 rpm, 10 minutes), were placed onto fresh 911 cells.

ticle, VP), and tested for contamination by PCR with specific primers for Ad40 E1, IX, IVa2 E3, fibers and E4orf2, luciferase reporter gene, and Ad5 E2 at 35 cycles (Table 4).

Confirmation of the genetic integrity of Ad40pΔE1-Luc vector produced by our method was first done by shotgun sequencing. More than 80% of the Ad40pΔE1-Luc sequence (88.8%, 30791 of 34685 bp) was covered by shotgun sequencing and was found to be identical to the expected sequence. The remaining portion of the Ad vector genome was sequenced by PCR with primers based on the known sequence. The restriction analysis of Ad40pΔE1-Luc with ClaI, HindIII, and SwaI agreed with the expected sequence.

TABLE 4

Sequences of primers used in this study.

| Assay | Primer | Location[a] | Sequence (5' to 3') |
|---|---|---|---|
| PCR | Ad40 E1 | F 418-437 | ACTCTTGAGTGCGAGCGAGT (SEQ ID NO:1) |
|  |  | R 3149-3129 | TTAATCCTCATCGCTGGATTC (SEQ ID NO: 2) |
| PCR | Ad40 E1/IX/IVa2 | F 1719-1736 | ATGGAGCGCCCAAACTCA (SEQ ID NO: 3) |
|  |  | R 4501-4482 | GTCATTGGGGTCATTTACGG (SEQ ID NO: 4) |
| PCR | Ad40 E3/short fiber | F 27035-27054 | TTCCTGCGCTAACGTAACCT (SEQ ID NO: 5) |
|  |  | R 29179-29198 | TAAAGCCTAACGCTCCGGTA (SEQ ID NO: 6) |
| PCR | Ad40 long fiber | F 29977-29996 | TGACTTCAACCCCGTCTACC (SEQ ID NO: 7) |
|  |  | R 30488-30469 | GGGGGCTAGAAAACAAAACC (SEQ ID NO: 8) |
| qPCR | Ad40 fiber for qPCR | F 30372-30394 | AACTTTCTCTCTTAATAGACGCC (SEQ ID NO: 9) |
|  |  | R 30489-30471 | AGGGGGCTAGAAAACAAAA (SEQ ID NO: 10) |
| PCR | Ad40 E4orf2 | F 33412-33431 | CGTGTCACCTGCAGTTCATT (SEQ ID NO: 11) |
|  |  | R 33740-33721 | CCTGAGCCCCTGATGTTTTA (SEQ ID NO: 12) |
| PCR | Ad5 E2 | F 22527-22546 | AAACTCAGGCACAACCATCC (SEQ ID NO: 13) |
|  |  | R 22867-22848 | ACCTTTTGATGCCACTACGG (SEQ ID NO: 14) |
| PCR, qPCR | Luciferase reporter gene | F 1395-1419 | CCGCCTGAAGTCTCTGATTAAGTAC (SEQ ID NO: 15) |
|  |  | R 1466-1446 | TGGAGCAAGATGGATTCCAAT (SEQ ID NO: 16) |
| qPCR | Murine GAPDH | F 649-668 | CCAGAACATCATCCCTGCAT (SEQ ID NO: 17) |
|  |  | R 715-695 | GTTCAGCTCTGGGATGACCTT (SEQ ID NO: 18) |

[a]The nucleotide positions of Ad40, Ad5, luciferase reporter gene, and murine GAPDH are based on GenBank (NCBI) accession sequence L19443, AY339865, U47295, and M32599, respectively. F, Forward; R, Reverse; qPCR, real-time PCR.

Figure 2:
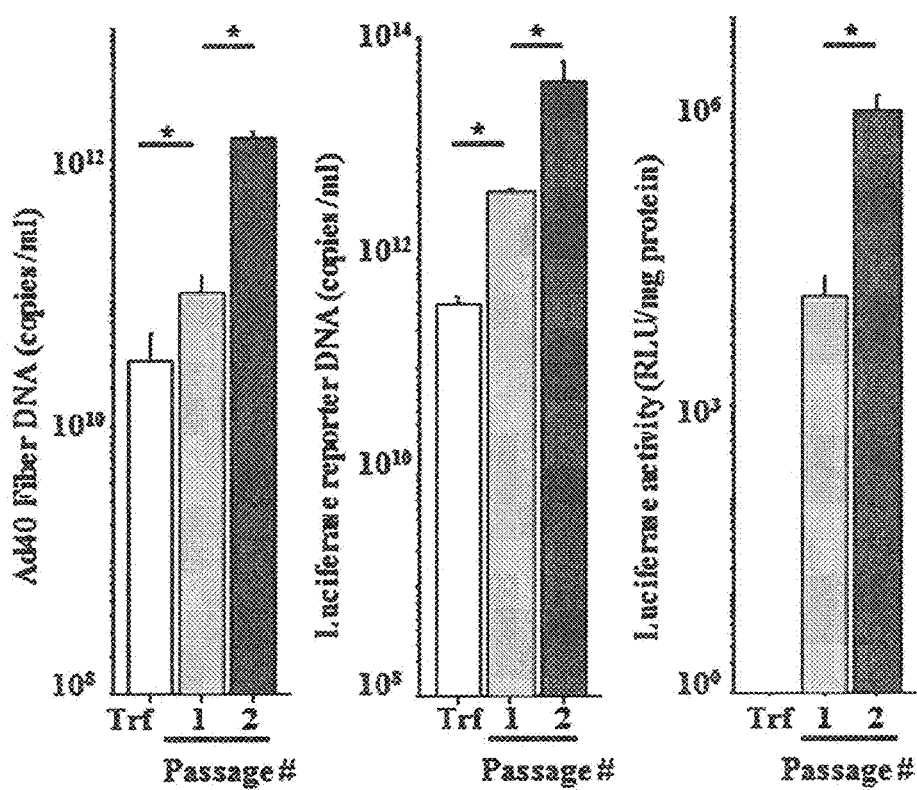
FIG. 2. Transduction of 911 cells with Ad40pΔE1-Luc. Representative data from duplicate experiments were shown. The results shown are mean values of triplicate. Error bars indicate the 95% confidence interval. Asterisks denote statistical significance ($P<0.05$). Trf, Transfection; RLU, relative luminescence units.

In order to make vectors suitable for in vivo studies, the same amplification was repeated using 1:3 dilutions of CVLs, which were prepared by centrifugation (1500 rpm, 10 minutes), three cycles of freeze-thawing of 1.7 mL suspension, and another centrifugation (3000 rpm, 10 minutes), until apparent cytopathic effect (CPE, grape-like clusters, and >90% cell detachment at the $2^{nd}$ passage) was observed in a 60-mm dish. The transduction of 911 cells with Ad40pΔE1-Luc was evaluated using CVL by the Ad vector copy number, which was measured by the real-time PCR for Ad40 fiber and luciferase reporter gene, and by cellular luciferase activity. Representative data from duplicate experiments were shown in FIG. 2. At every round of infection, the Ad vector copy number and luciferase activity were assessed by Real-time PCR and luciferase assay, respectively and found to increase about one order of magnitude. After observing obvious CPE, the vectors were amplified subsequently in 911 cells ($4 \times 10^4$ cells/cm$^2$) in a 100 mm dish, a 75 cm$^2$ flask, or 1, 2, 4, 8, and 16 175-cm$^2$ flasks for subsequent CsCl centrifugation ($10^{th}$ passage) according to standard methodology (Yamasaki et al., 2010 Arch Virol 155:1059-1068).

Vectors were purified with double CsCl centrifugation, titered with the optical density at 260 nm ($OD_{260}$; virus par- Cell Lines.

The 911 cells (a kind gift from Dr. Alex J. van der Eb, Leiden University, Leiden, Netherlands) were maintained as adherent cultures in Dulbecco modified Eagle medium (DMEM, Mediatech, Inc., Manassas, Va.) supplemented with 5-10% fetal bovine serum (FBS, HyClone, Logan, Utah), 2 mM L-glutamine (Mediatech, Inc.), and 100 IU/mL penicillin and 100 μg/mL streptomycin (Invitrogen, Carlsbad, Calif.). The human colorectal adenocarcinoma cells (CaCo-2, HTB-37, American Type Culture Collection, Manassas, Va.) were grown in DMEM supplemented with 15% FBS, 1% nonessential amino acids (Invitrogen), 100 IU/mL penicillin and 100 μg/mL streptomycin. After reaching 80-90% confluence, undifferentiated CaCo-2 cells were trypsinized and seeded at low density. Differentiated CaCo-2 cells were used at postconfluence after 21 days of culture, refreshing medium every two days as previously described. Cells were grown in a dedicated virus free incubator at 37° C. in a humidified atmosphere containing 5% $CO_2$.

Vector Production.

Ad40pΔE1-Luc, Ad40pΔE1-CMV-Luc, and Ad40pΔE1-CMV-Ova were generated, as illustrated in FIG. 1, by homologous recombination between a ClaI-digested plasmid encoding wild type AD40 into and a rescue plasmid. The rescue plasmids contained either a non-promoter-driven firefly luciferase reporter gene (for AD40ΔE1-Luc), a CMV-promoter (pCEP4, Invitrogen)-driven firefly luciferase reporter gene (pGL3-Basic Vector, Promega, Madison, Wis.), or a CMV-promoter-driven ovalbumin gene (Ova, cloned by reverse transcription PCR from E.G7 thymoma cell RNA) in *E. coli* BJ5183 (Stratagene, La Jolla, Calif.). The resultant plasmid was amplified with DH5alpha (Invitrogen, Grand Island, N.Y.).

Vectors were generated by transfection using Superfect (Qiagen, Valencia, Calif.). All transfection and infection were performed in a dedicated Ad40 work incubator isolated from other viruses, especially Ad5. Vectors were titered with $OD_{260}$, and PFU and $TCID_{50}$ (AdEasy Application Manual; Qbiogene, Carlsbad, Calif.) assays, and tested for contamination by PCR (QIAGEN fast cycling PCR kit, Qiagen, Germantown, Md.). The PCR was performed on a 9700 thermocycler (Applied Biosystems, Foster City, Calif.) with specific primers for Ad40 E1, IX, IVa2 E3, fibers and E4orf2, luciferase reporter gene, and Ad5 E2 at 35 cycles. Subsequently, the PCR fragments were cloned and sequenced as previously described (Yamasaki et al., 2010 Arch Virol 155: 1059-1068). Ad5-CMV-Luc was built by the homologous recombination between pShuttle including CMV promoter and firefly luciferase reporter gene, and pAdEasy-1 (Stratagene) as previously described (Luo et al., 2007 Nat Protoc 2:1236-1247).

Mice.

All animal experiments were conducted with approval from the Institutional Animal Care and Use Committee, University of Minnesota (Minneapolis, Minn.). In all cases, 6-8-week-old female BALB/c or C57BL/6 mice (Harlan Laboratories, Inc.; Madison, Wis.) were utilized.

In Vitro Human Microfold Cell Model.

The in vitro microfold cell model was made as previously described (Kernels et al., 1997 Science 277:949-952; Tyrer et al., 2002 Biochem Biophys Res Commun 299:377-383). Briefly, transwells with 3 μm pores (Corning Life Sciences, Lowell, Mass.) were inverted into 150-mm dishes, seeded with 100 μL CaCo-2 medium containing $3.0 \times 10^5$ CaCo-2 cells. The cells were left overnight (16-20 hours) at 37° C. in 5% $CO_2$ incubator. The supports were reverted and placed back into their 24-well plates, then 600 μL medium was added to the wells, and 100 μL culture medium was added to the inner chambers. The cells were incubated at 37° C. in 5% $CO_2$ incubator. Medium were changed every two days. The cells were left to fully differentiate for 21 days. The transepithelial electrical resistance of the CaCo-2 cultures was measured with an EVOM epithelial voltohmmeter (World Precision Instruments, Sarasota, Fla.) to confirm their fully differentiated state. Cultures displaying a transepithelial resistance greater than 150 ohm $cm^2$ were enterocyte-like cells. BALB/c mice were euthanized using carbon dioxide gas. The nubbins of PPs' tissues were secured and viable cells evaluated by trypan blue staining were obtained from each mouse as previously described (Lefrançois and Lycke, 1996 "Isolation of mouse small intestinal intraepithelial lymphocytes, Peyer's patch, and lamina propria cells," in *Curr Protoc Immunol;* 3.19.1-3.19.16). PP cells were resuspended in CaCo-2 medium at a concentration of $10^7$ cell/mL. Medium was aspirated from the apical chamber of the CaCo-2 cells on Transwells and replaced with 600 μL CaCo-2 medium. The medium of the basolateral chambers were replaced with 100 μL PP cell suspension ($10^6$ cells). The cultures were incubated at 37° C. in 5% $CO_2$ incubator for 2 days and then examined.

DNA Extraction and Real-Time PCR-Based Assay.

After a DNase treatment step to eliminate nonencapsidated DNA (Thomas et al., 2007 Methods Mol Med 130:185-192), viral DNA was purified by a QIAamp DNA blood mini kit (Qiagen, Germantown, Md.) from the 200 μl CVLs which were prepared by three freeze-thaw cycles and centrifugation (3000 rpm, 10 minutes) or tissues surgically excised from mice. In order to compare the DNA copy numbers between Ad40pΔE1-Luc, Ad40pΔE1-CMV-Luc, and Ad5-CMV-Luc, previously published primers for Ad40 fiber, luciferase reporter gene (Pringle et al., 2005 Gene Ther 12:1206-1214), and murine GAPDH were used in real-time PCR analysis by SYBR green technology. The real-time SYBR green PCR assay was performed using a QuantiTect SYBR green PCR kit (Qiagen, Germantown, Md.) in an ABI sequence detection system (ABI PRISM 7400, Applied Biosystems, Carlsbad, Calif.) and each experiment was conducted in triplicate. PCR-cloned Ad40 fiber, luciferase reporter, or murine GAPDH was used as copy number standards. The lower limit of detection was $10^7$ copies/mL of PCR-cloned Ad40 fiber DNA and $10^7$ copies/mL or copies/cell of PCR-cloned luciferase reporter DNA, and the lower limit of quantification was $10^8$ copies/mL or copies/cell. The lower limit of the relative luciferase reporter DNA was determined to be one luciferase reporter DNA copy per $10^4$ GAPDH DNA copies based on the control results. Template-negative samples served as controls for realtime PCR and were always sub-detectable.

Ad Vector Binding Assay.

To analyze vector-cell binding, cells were seeded at $5.0 \times 10^4$ cells or $3.0 \times 10^5$ CaCo-2 cells (for differentiated CaCo-2 at postconfluence after 21 days of culture) per well in 24-well plates. After 24 hours, CaCo-2 cells were infected with 2000 VP/cell in 100 μL of each growth medium and incubated for one hour at 4° C. Cells were washed with phosphate-buffer saline (PBS) three times, scraped from the plates and processed with a QIAamp DNA Blood Mini Kit (Qiagen, Germantown, Md.). The isolated DNA was analyzed by real-time PCR analysis to determine the luciferase reporter DNA copy number with luciferase-specific primers described above. All of experiments were repeated in three independent experiments.

In Vitro Luciferase Assay.

Transcriptional activity of Ad vectors was assessed via luciferase activity assays in undifferentiated and differentiated CaCo-2, and in vitro M cell model. Luciferase protein levels were assessed using a Luciferase assay system (Promega, Madison, Wis.). The results were read using FLUOstar Omega (BMG LABTECH, Durham, N.C.) and readings were normalized to total protein concentration as determined by a DC protein assay (Bio-Rad Laboratories, Hercules, Calif.).

In Vitro Effect of a Pepsin Treatment.

For evaluating the effect of a pepsin treatment, Ad40pΔE1-CMV-Luc and Ad5-CMV-Luc were treated with 0.1M HCL and 2.5 mg/mL pepsin from porcine gastric mucosa (Sigma, St. Louis, Mo.) for five minutes at 37° C., neutralized with 10× Tris-Hepes buffer (200 mM Tris, 500 mM HEPES, and 1.5 M NaCl), diluted with an equal amount of culture medium, adjusted pH to 7 with 1 M NaOH, and applied to cells for Ad vector binding and in vitro luciferase assay described above.

Oral Administration.

The mice were anesthetized with 2-5% isoflurane after prohibiting the access to food for two hours prior to anesthesia. Oral gavage was performed using a ball ended feeding needle (FTP-20-30, Instech Solomon, Plymouth Meeting, Pa.). The distance that the needle needs to be inserted into the mice was estimated, marked it on the needle, restrained the anesthetized mice with the head and body extended as straight as possible to facilitate introduction of the gavage needle, introduced the needle in the space between the left incisors and molars, and gently swallowed as the feeding tube approaches the pharynx, facilitating entry into the esophagus. Once the desired position was attained, 100 µL PBS (control), or $10^{10}$ VP of Ad40pΔE1-CMV-Luc or Ad5-CMV-Luc diluted 100 µL PBS were injected and withdrawn the syringe. The mice were monitored after the procedure to ensure that there was no adverse effect every day until 48 hours after vector administration.

Intraduodenal Administration.

Following two hours of fasting, the intraduodenal administration was accomplished by aseptically opening the abdomens of mice anaesthetized with isoflurane and injecting 100 µL PBS (control), or $10^{10}$ VP of Ad40pΔE1-CMV-Luc or Ad5-CMV-Luc diluted 100 µL PBS with a 30 gauge needle into the lumen of the duodenum (1 cm downstream of the stomach). The abdominal wall and skin was closed using 3-0 Nylon sutures, monitored, and observed until 48 hours after vector administration.

In Vivo Biodistribution.

After 48 hours post oral or intraduodenal administration, murine duodenum (only for oral administration), jejunum without PPs (2 cm median part of the small intestine without macroscopically visiable PPs), ileum without PPs (2 cm upstream of the cecum without visible PPs), ileal with PPs (visible PPs observed for the first time at the upstream of the cecum), colon (2 cm downstream of the cecum), mesenteric lymph nodes, and spleen were isolated, DNA was purified by a QIAamp DNA blood mini kit, and then relative luciferase copy number (luciferase reporter DNA copies per GAPDH DNA copies) in the tissues were analyzed by real-time PCR (in three independent experiments). In at least two independent experiments, tissues were fixed with 4% paraformaldehyde in PBS, embedded in paraffin wax, sectioned at 3 µm, and stained sequentially with hematoxylin and eosin, and immunohistochemistry for luciferase proteins.

Immunohistochemistry.

Luciferase proteins in murine tissues after oral and intraduodenal administration were detected using a 1:100 dilution of a primary goat anti-luciferase (Promega, Madison, Wis.) antibody and a 1:200 dilution of secondary polyclonal rabbit anti-goat IgG-HRP (Dako, Glostrup, Denmark). Immunohistochemistry was performed with an EnVision+ system-HRP/DAB (Dako, Glostrup, Denmark). Formalin-fixed paraffin-embedded tissue sections were sequentially deparaffinized, rehydrated, boiled in 0.1 M citrate buffer (pH 6.0, Dako, Glostrup, Denmark) for antigen retrieval, and blocked for non-specific activity with 1% bovine serum albumin (Sigma, St. Louis, Mo.) and protein block serum-free (Dako, Glostrup, Denmark). Incubation with primary antibody was performed overnight at 4° C. After a brief rinse in PBS with 0.1% Tween 20, the sections were incubated with secondary antibody for 30 minutes and with DAB+ substrate-chromogen solution (Dako, Glostrup, Denmark) at room temperature. The slides were mounted in Glycergel Mounting Medium (Dako, Glostrup, Denmark). The histologies of murine tissues were assessed with hematoxylin and eosin staining of slides. All staining and sections were performed in at least two independent experiments. All slides were scanned at ×100, ×200, and ×400 magnification using aNikon Eclipse TS100 microscope (Nikon, Melville, N.Y.). The primary antibody was omitted on the slides that served as negative controls and were always no detectable.

Statistical Analysis.

Continuous variables were compared by Mann-Whitney-U test. All P-values were 2-sided, and the type I error rate was fixed at P<0.05.

Example 2

Cell Lines

The Pan02 murine pancreatic adenocarcinoma cell line obtained from the National Cancer Institute and EL4 (ATCC TIB-39; American Type Culture Collection, Manassas, Va.) are grown in RPMI 1640 (Mediatech, Inc., Manassas, Va.) supplemented with 10% fetal bovine serum, 2 mM L-glutamine (Mediatech, Inc.), 1 mM sodium pyruvate (Invitrogen, Carlsbad, Calif.), and 100 IU/mL penicillin and 100 µg/mL streptomycin (Invitrogen, Carlsbad, Calif.). Cells are grown in a designated virus-free incubator at 37° C. in a humidified atmosphere containing 5% $CO_2$.

Ova-expressing, LuciGFP-expressing, or Msln-expressing Pan02 cell line (Pan02-Ova, Pan02-LuciGFP, or Pan02-Msln) are generated by transducing Pan02 with pMX-Ova-puro, pMX-LuciGFP-puro, or pMX-Msln-puro using Lipofectamine 2000 (Tnvitrogen, Carlsbad, Calif.). The Ova or Msln expression in Pan02-Ova or Pan02-Msln is evaluated by Western blotting. The Msln or GFP expression in Pan02-Msln or Pan02-LuciGFP is also observed by flow cytometry and immunocytofluorescence. The Luc expression in Pan02-LuciGFP is detected by Luciferase assay system (Promega, Madison, Wis.).

Mice.

All animal experiments are conducted with approval from the Institutional Animal Care and Use Committee, University of Minnesota (Minneapolis, Minn.). In all cases, 6-8-week-old female C57BL/6 mice (Harlan Laboratories, Inc.; Madison, Wis.) are utilized.

Intraduodenal Administration.

Following two hours of fasting, the intraduodenal administration is accomplished by aseptically opening the abdomens of mice under anesthesia with isoflurane and injecting 100 µL PBS (control), or 1010 VP of Ad40pΔE1-CMV-Luc, Ad40pΔE1-CMV-Ova, Ad40pΔE1-CMV-Msln, Ad5-CMV-Luc, or Ad5-CMV-Ova diluted 100 µL PBS with a 30 gauge needle into the lumen of the duodenum (1 cm downstream of the stomach). The abdominal wall and skin are closed using 4-0 Nylon sutures. Mice are monitored and observed every day until sacrifice for any adverse effects.

Enzyme-Linked Immunosorbent Assay (ELISA) for Ova-Specific Ig, IgG1, and IgG2a.

Blood samples are obtained by cardiac puncture in heparin-coated syringes immediately following sacrifice on day 14 after intraduodenal administration of five groups (PBS (control), or $10^{10}$ VP of Ad40pΔE1-CMV-Luc, Ad40pΔE1-CMV-Ova, Ad5-CMV-Luc, or Ad5-CMV-Ova). The samples are allowed to clot at 37° C. for three hours and the clot is removed by centrifuging for five minutes at 100,000 rpm at 4° C. The supernatant (serum) is stored at −80° C.

Fecal pellet samples are collected and extracted by making a 1/10 suspension (w/v) with PBS plus protease inhibitor (Complete protease inhibitor cocktail EDTA-free mini tablet, Roche Applied Science, Mannheim, Germany). After the suspension is vortexed and spun for 10 minutes at 14000 rpm, the supernatant is collected and stored at −80° C.

Sera and feces are tested at 1/10 (for feces), 1/100, and 1/1000 (for sera), and total Ig, IgG1 (for sera), and IgG2a (for sera) titers are calculated with respect to controls present in each enzyme-linked immunosorbent assay plate (Mouse Anti-Ovalbumin Ig's, IgG1, or IgG2a ELISA Kit, Alpha diagnostic international, San Antonio, Tex.). Results are presented as activity units, which correspond to controls that gave an enzyme-linked immunosorbent assay reading greater than the threshold value (optical density >0.3).

Intracellular IFN-γ Staining and Flow Cytometry.

Splenocytes are harvested from mice on day 14 after intraduodenal administration. Prior to intracellular IFN-γ staining, splenocytes ($2 \times 10^6$/mL) are incubated with 10 µg/mL of OVA peptide (SIINFKL, H-2Kb; ProImmune Ltd., Oxford, UK), Msln peptides ($Meso_{351-359}$, $Meso_{612-619}$), Pan02-Ova or Pan02-Msln cell lysate. Lysates are generated by four freeze-thaw cycles, passed through a 0.22-µm filter, and total protein concentration as determined by a DC protein assay (Bio-Rad Laboratories, Hercules, Calif.) in RPMI 1640 (Mediatech, Inc., Manassas, Va.) supplemented with 10% fetal bovine serum, 2 mM L-glutamine (Mediatech, Inc.), 1 mM sodium pyruvate (Invitrogen, Carlsbad, Calif.), and 100 IU/mL penicillin and 100 µg/mL streptomycin (Invitrogen, Carlsbad, Calif.) for 16 hours. BD GolgiPlug (BD Biosciences, San Jose, Calif.) is added for five hours of culture. After surface staining with anti-CD3e, CD4, CD8a, or NK1.1 (BD Biosciences, San Jose, Calif.), cells are stained with anti-IFN-γ using Cytofix/Cytoperm kit (BD Biosciences, San Jose, Calif.). The regulatory T cells are identified as $CD4^+$/$CD25^+$/$FOXP3^+$ cells using Foxp3 Staining Buffer Set (eBioscience, Inc. San Diego, Calif.).

Cells isolated from Peyer's patches (PPs), mesenteric lymph nodes (MLN), and spleen on day 14 after intraduodenal administration of 5 groups (PBS (control), or $10^{10}$ VP of Ad40pΔE1-CMV-Luc, Ad40pΔE1-CMV-Ova, Ad5-CMV-Luc, or Ad5-CMV-Ova) are negatively selected with $CD8a^+$ T cells isolation kit (MACS; Miltenyi Biotec, Auburn, Calif.). The combined PPs, MLN, or spleen from each experiment of five mice are used. The Ova-specific $CD8a^+$ T cells are analyzed after pro5 MHC Pentamer H-2Kb/SIINFEKL (SEQ ID NO:23) (ProImmune Ltd., Oxford, UK), followed by surface staining with anti-CD8a and CD19. Over $2 \times 10^5$ events are acquired on a FACSCalibur (BD Biosciences, San Jose, Calif.). Data are analyzed using CellQuest (BD Biosciences, San Jose, Calif.) and FlowJo (TreeStar Inc., Ashland, Oreg.) software. Cells in the lymphocyte gate are used for analysis. As a negative control, cells are stained with isotype controls.

In Vivo Cytotoxic T-Cell Assay.

C57BL/6 splenocytes ($5 \times 10^6$/mL) are incubated for 90 minutes at 37° C. with or without 1 µg/mL of OVA peptide (SIINFKL (SEQ ID NO:23, H-2Kb; ProImmune Ltd., Oxford, UK) and labeled for 10 minutes at 37° C. with carboxyflurescein diacetate succinimidyl diester (CFSE, Molecular Probes, Life Technologies Corp., Carlsbad, Calif.) at 5 µM ($CFSE^{hi}$, peptide-labeled splenocytes) or 0.5 µM ($CFSE^{lo}$, splenocytes without peptide). Immunized or naïve control mice after intraduodenal administration on day 14 after intraduodenal administration of 5 groups (PBS (control), or $10^{10}$ VP of Ad40pΔE1-CMV-Luc, Ad40pΔE1-CMV-Ova, Ad5-CMV-Luc, or Ad5-CMV-Ova) are injected intravenously with $10^7$ cells of each fraction. Splenocytes are isolated 20 hours later, and analyzed by flow cytometry. Specific cytotoxicity is calculated with the following equation:

$$\text{cytotoxicity}(\%) = [1 - (\text{ratio immune}/\text{ratio naïve})] \times 100;$$

where ratio=percentage of $CFSE_{hi}$/percentage of $CFSE_{lo}$. Over $1 \times 10^6$ events are acquired for further CESF analysis.

Immunofluorescence Staining.

Frozen sections (6 µm-10 µm) are cut on a cryostat and prepared for Luc or Msln staining experiments. After the evaluation of tissues using hematoxylin and eosin stain, the sections are fixed with 4% paraformaldehyde/phosphate buffered saline (PBS) at 4° C. for 10 minutes and blocked with 1% BSA in 0.1% Tween20-PBS. Primary Abs is applied overnight at 4° C. Primary goat Abs is detected by Tetramethyl Rhodamine Isothiocyanate (TRITC, Jackson ImmunoResearch Laboratories, Inc., West Grove, Pa.). DAPI (Vector Laboratories, Inc. Burlingame, Calif.) is used as a nuclear counterstain. Images are acquired using a confocal spectral imaging microscope systems (Nikon) and edited when necessary with Photoshop (Adobe Systems).

Prophylactic and Therapeutic Tumor Studies in Subcutaneous Tumor Model.

For the prophylactic study, on day 14 after intraduodenal administration of 3 groups (PBS (control), or $10^{10}$ VP of Ad40pΔE1-CMV-Ova, or Ad5-CMV-Ova), mice are challenged with Pan02-Ova or Pan02-LuciGFP cells injected subcutaneously into the right inguinal flank with $5 \times 10^5$ viable cells per mouse. Mice are monitored and weighed twice weekly. Tumor growth is monitored with fine calipers and tumor volumes are calculated using the following equation:

$$\text{volume (mm}^3) = A \times B \times 0.5236,$$

where A is the largest dimension and B is the diameter perpendicular to A.

On day 28 after tumor challenge or once the tumors exceed a diameter of 1 cm, splenocytes and tumor infiltrating lymphocytes are analyzed by flow cytometry, and blood and fecal samples are harvested for ELISA analysis.

For the therapeutic study, the viruses are administered 1 week after tumor inoculation.

Prophylactic and Therapeutic Studies in Orthotopic Tumor Model.

For the prophylactic study, two weeks after intraduodenal administration on day 14 after intraduodenal administration of 3 groups (PBS (control), or $10^{10}$ VP of Ad40pΔE1-CMV-Ova, or Ad40pΔE1-CMV-Msln), mice are challenged with $2.5 \times 10^5$ viable Pan02-LuciGFP cells per mouse injected into pancreas using a 30 gauge needle after a small laparotomy is performed exposing the inferior pole of the spleen and tail of the pancreas, which are externalized through the wound. The skin and abdominal musculature are closed with 4-0 Nylon sutures. Mice are monitored and weighed twice weekly. Tumor growth is monitored with bioluminescence imaging. Briefly, mice are anaesthetized with isofluorane (Hospira, Lake Forest, Ill.), injected with 15 mg/mL D-luciferin (Molecular Imaging Products, Bend Oreg.), and imaged 15 minutes later with a CCCD camera (IVIS, Xenogen, Mass.). After acquiring a grey scale photograph, a bioluminescent image is obtained using 20 cm field of view, binning factor of 8, 1/f stop, and open filter using a four-minute exposure. Regions of interest (ROIs) are defined manually (using a whole mouse area in each case), signal intensities are calculated using the Living Image software (Xenogen) and expressed as photons per second. Background photon flux is defined from a ROI drawn over a control mouse to which no Pan02-LuciGFP is administered. On day 28 after tumor challenge, splenocytes and tumor infiltrating lymphocytes are analyzed by flow cytometry, blood and fecal samples are harvested for ELISA analysis, and tumor tissues are frozen for immunofluorescence staining.

For the therapeutic study, the viruses are administered 1 week after tumor inoculation.

Statistical Analysis.

Continuous variables are compared by Mann-Whitney-U test or Kruskal-Wallis test. All P-values are 2-sided, and the type I error rate is fixed at $P < 0.05$.

Example 3

In Vivo Immunological Reaction

In vivo immunological reaction induced by Ad40 vector are assessed in mice using either an ovalbumin (Ova)-expressing vector and/or mesothelin-expressing vector. Ova is a commonly used model antigen for evaluating genetic vaccines in mouse models. Humoral and cellular immune-response are analyzed. Mesothelin is a clinically relevant antigens associated with pancreatic cancer and mesothelioma.
Antibody Production After Intraduodenal Administration of Ad40-Ova or Ad40-Mesolthelin.

After intraduodenal administration of either Ad40-Ova or Ad40-mesothelin vectors, production of anti-Ova antibodies and anti-mesothelin antibodies in the serum and feces are analyzed by ELISA and the subtype(s) of the immunoglobulins produced are determined.
Cytokine Production After Intraduodenal Administration of Ad40-Ova or Ad40-Mesolthelin.

IFN-γ staining, surface marker expression, and Ova-specific pentamer binding were analyzed as described in Example 2 fourteen days post intraduodenal administration of $10^{10}$ viral particles of Ad40-Ova per mouse (6-to-7-week-old female B6 mice (n=5 in each experiment)).

Results are shown in FIG. 7. In the $CD8^+/CD19^-$ population in the immunized mouse spleen, 56.2% of the cells showed specific reactivity to Ova-specific pentamer. This is indicative of induction of cellular immune response by Ad40 vector against Ova.

IFN-γ staining and surface marker expression are analyzed in mice immunized with the Ad40-mesolthelin vector.
In Vivo Cytotoxicity Assay after Intraduodenal Administration of Ad40-Ova or Ad40-Mesolthelin.

In vivo cytotoxicity assay is performed as described in Example 2 with splenocytes from the mice receiving either Ad40-Ova or Ad40-mesothelin as an effector and splenocytes loaded with Ova peptide or Msln peptide, respectively, as the target.

Example 4

Prophylactic Tumor Treatment

Prophylactic tumor treatment is evaluated using either Ad40-Ova vector or Ad40-mesothelin vector compared against a control vector using an Ova-expressing Pan02 cell line or Msln-expressing vector, respectively.
Therapeutic Tumor Treatment.

Therapeutic tumor treatment is evaluated using either Ad40-Ova vector or Ad40-mesothelin vector compared against a control vector using an Ova-expressing Pan02 cell line or Msln-expressing vector, respectively.
Anti-Tumor Effect of Ad40-Based Vaccine.

Anti-tumor effect of Ad40-based vaccine is assessed with ovalbumin and mesothelin as antigen. The anti-tumor effect of an Ad40-based vaccine is assessed with either an Ova-expressing Pan02 mouse pancreatic cancer cell-based syngeneic model or a Msln-expressing Pan02 mouse pancreatic cancer cell-based syngeneic model, as described in Example 2.

Example 5

RNA Extraction

Total RNA was isolated from the cell pellets using an RNeasy mini kit (Qiagen, Germantown, Md.). Contaminating DNA was removed by RNase-free DNase (Qiagen, Germantown, Md.). One and a half micrograms of total RNA was reverse transcribed using an Omniscript RT kit (Qiagen, Germantown, Md.) with random hexamers (Applied Biosystems, Carlsbad, Calif.). The subsequent PCR was performed with specific primers as previously published.
DNA Extraction and Real-Time PCR-Based Assay.

After a DNase treatment step to eliminate nonencapsidated DNA, viral DNA was purified by a QIAamp DNA blood mini kit (Qiagen, Germantown, Md.) from the 200 µL CVLs, which were prepared by three freeze-thaw cycles and centrifugation (3000 rpm, 10 minutes), or tissues surgically excised from mice. In order to compare the DNA copy numbers among rAd40pΔE1-Luc, rAd40pΔE1-CMV-Luc, and rAd5-CMV-Luc, previously published primers for Ad40 fiber (Yamasaki et al., 2010 Arch. Virol. 155:1059-1068), luciferase reporter gene, and mouse GAPDH were used in real-time PCR analysis by SYBR green method. The real-time PCR assay was performed using a QuantiTect SYBR green PCR kit (Qiagen, Germantown, Md.) with an ABI sequence detection system (ABI PRISM 7400, Applied Biosystems, Calrsbad, Calif.) and each experiment was conducted in triplicate. PCR-cloned Ad40 fiber, luciferase reporter, and mouse GAPDH fragments were used as copy number standards. The lower limit of detection was $10^7$ copies/mL of PCR-cloned Ad40 fiber DNA and $10^7$ copies/mL or copies/cell of PCR-cloned luciferase reporter DNA, and the lower limit of quantification was $10^8$ copies/mL or copies/cell. The lower limit of the relative luciferase reporter DNA was determined to be one luciferase reporter DNA copy per $10^4$ GAPDH DNA copies based on the control results. Template-negative samples served as controls for real-time PCR and were always sub-detectable.
Cell Lines.

The 911 cells (a kind gift from Dr. Alex J. van der Eb, Leiden University, Leiden, Netherlands; Yamasaki et al., 2010 Arch. Virol. 155:1059-1068; Fallaux et al., 1996 Hum. Gene Ther. 7:215-222) and the human colorectal adenocarcinoma cells (CaCo-2, HTB-37; American Type Culture Collection, Manassas, Va.; Hubatsch et al., 2007 Nat. Protoc. 2:2111-2119) were maintained as previously described. The Pan02 mouse pancreatic adenocarcinoma cells (Corbett et al., 1984 Cancer Res. 44:717-726) were obtained from the National Cancer Institute. For the generation of plasmid encoding chicken ovalbumin (pMX-Ova-puro), pMX-puro was kindly provided by Dr. Toshio Kitamura of the University of Tokyo. The DNA fragments encoding Ova were first amplified by reverse-transcription (RT)-PCR using RNA samples from E.G7 thymoma tumor (kindly provided by Dr. Matthew F. Mescher of the University of Minnesota). The Ova-expressing Pan02 cell line (Pan02-Ova) was generated by transducing Pan02 with pMX-Ova-puro using Lipofectamine 2000 (Invitrogen, Carlsbad, Calif.), selected and maintained by Puromycin (2 µg/mL), and evaluated by western blotting. The in vitro M-cell model was made as previously described (Kernéis et al., 1997 Science 277:949-952; Tyrer et al., 2002 Biochem. Biophys. Res. Commun. 299: 377-383).
Ad Vector Binding Assay.

To analyze vector-cell binding, cells were seeded at $5 \times 10^4$ cells per well in 24-well plates or at $3 \times 10^5$ CaCo-2 cells for differentiated CaCo-2 at postconfluence after 21 days of culture. After 24 hours, CaCo-2 were infected and incubated for one hour at 4° C. Cells were washed with phosphate-buffer saline (PBS) three times, scraped from the plates, and processed with a QIAamp DNA Blood Mini Kit (Qiagen, Germantown, Md.). The isolated DNA was analyzed by real-time PCR analysis to determine the luciferase reporter DNA copy number with luciferase-specific primers.

Western Blot.

The cell pellets were lysed with sample buffer (0.125 M Tris-HCl, pH 6.8, 2% SDS, 5% β-mercaptoethanol, 10% glycerol) plus protease inhibitor (Complete protease inhibitor cocktail EDTA-free mini tablet, Roche Applied Science, Mannheim, Germany) for 30 minutes on ice with gentle vortexing. After homogenization on ice by multiple passages through a 26-gauge needle, cellular debris was removed by centrifugation (14000 rpm, 10 minutes) at 4° C. Subsequent to denature for five minutes at 95° C., the lysates were separated by 10% SDS-polyacrylamide gel electrophoresis and transferred to PVDF membranes (Bio-Rad Laboratories, Inc., Hercules, Calif.). The membranes were blocked for one hour at 4° C. with 5% nonfat dry milk in 0.05% Tween 20-PBS, and probed with primary antibody (mouse monoclonal anti-Ova antibody, 1:100 dilution, 3G2E1D9; Santa Cruz Biotechnology, Inc.; Santa Cruz, Calif.: mouse monoclonal anti-beta-actin antibody, 1:10000, AC-15, Sigma-Aldrich, St Louis, Mo.), diluted in 0.05% Tween20-PBS overnight at 4° C. Membranes were then incubated with a horseradish peroxidase conjugated sheep anti-mouse antibody (GE Health, Piscataway, N.J.) diluted in 0.05% Tween20-PBS for one hour at 4° C., developed by chemiluminescence (ECL plus, GE Health), and exposed to KODAK BioMax MR Film (Carestream Health, Inc.; Rochester, N.Y.). The beta-actin was used as an internal control to adjust for differences in the amount of protein loaded in each lane.

In Vitro Luciferase Assay.

Transgene expression of rAd was assessed via luciferase activity assays in undifferentiated and differentiated CaCo-2, and the in vitro M-cell model. Luciferase protein levels were assessed using a Luciferase assay system (Promega, Madison, Wis.). The results were read with FLUOstar Omega (BMG LABTECH, Durham, N.C.), and readings were noimalized to total protein concentration as determined by a DC protein assay (Bio-Rad Laboratories, Inc., Hercules, Calif.).

In Vitro Model of Human Microfold Cells.

The in vitro M-cell model was made as previously described (Kernéis et al., 1997 Science 277:949-952; Tyrer et al., 2002 Biochem. Biophys. Res. Commun. 299:377-383). Briefly, transwells with 3 μm pores (Corning Life Sciences, Lowell, Mass.) were placed invertedly in 150-mm dishes, then seeded with 100 μL CaCo-2 medium containing $3.0 \times 10^5$ CaCo-2 cells. The cells were incubated overnight (16-20 hours) at 37° C. in 5% $CO_2$ incubator. The supports were reverted and placed back into their 24-well plates, then 600 μL medium was added to the wells, and 100 μL of culture medium was added to the inner chambers. The cells were incubated at 37° C. in 5% $CO_2$ incubator with medium changed every two days. The cells were cultured for 21 days to allow differentiation. The transepithelial electrical resistance of the CaCo-2 cultures was measured with an EVOM epithelial voltohmmeter (World Precision Instruments, Sarasota, Fla.) to confirm their fully differentiated state. Cultures displaying a transepithelial resistance greater than 150 ohm $cm^2$ were considers as enterocyte-like cells. BALB/c mice were euthanized using carbon dioxide gas. The nubbins of PPs' tissues were harvested and viable cells evaluated by trypan blue staining were obtained from each mouse as previously described (Lefrancois and Lycke, 1996 "Isolation of mouse small intestinal intraepithelial lymphocytes, Peyer's patch, and lamina propria cells," in Curr. Protoc. Immunol. 3.19.1-3.19.16). PP cells were resuspended in CaCo-2 medium at $10^7$ cell/mL. Medium was aspirated from the apical chamber of the CaCo-2 cells on transwells and 600 μL CaCo-2 medium was added. The medium of the basolateral chambers were replaced with 100 μL PP cell suspension ($10^6$ cells). The cultures were incubated at 37° C. in 5% $CO_2$ incubator for two days before being used for analyses.

In Vitro Effect of Pepsin Treatment.

For evaluating the effect of pepsin treatment, rAd40pΔE1-CMV-Luc and rAd5-CMV-Luc were treated with 0.1M HCL and 2.5 mg/mL pepsin from porcine gastric mucosa (Sigma-Aldrich, St. Louis, Mo.) for five minutes at 37° C., neutralized with 10× Tris-Hepes buffer (200 mM Tris, 500 mM HEPES, and 1.5 M NaCl; Wang et al., 2009 J. Virol. 83:7166-7175), diluted with an equal amount of culture medium, adjusted pH to 7 with 1 M NaOH, and applied to cells for Ad vector binding and in vitro luciferase assay.

Intraduodenal Administration.

Following four hours of fasting for reducing the food in the duodenum, intraduodenal administration was accomplished by aseptically opening the abdomens of C57BL/6 (B6) or BALB/c (for diarrhea and anaphylaxis models) mice anaesthetized with isoflurane followed by injecting 100 μL PBS (control), or $10^{10}$ VP of rAd40pΔE1-CMV-Luc, rAd40pΔE1-CMV-Ova, rAd5-CMV-Luc or rAd5-CMV-Ova diluted to PBS with a 29½-gauge needle into the lumen of the duodenum (1 cm downstream of the stomach). The abdominal wall and skin was closed by suture.

Oral Administration.

The B6 mice were anesthetized with 2-5% isoflurane after prohibiting the access to food for four hours to limit foods in the stomach. Oral gavage was performed using a ball ended feeding needle (FTP-20-30, Instech Solomon, Plymouth Meeting, Pa.). The distance that the needle needs to be inserted into the mice was marked on the needle. The anesthetized mice were restrained in the position with the head and body extended as straight as possible, and the gavage needle was introduced into the space between the left incisors and molars, and gently swallowed as the feeding tube approaches the pharynx, facilitating entry into the esophagus. Once the desired position was attained, 100 μL PBS (control), or $10^{10}$ VP of rAd40pΔE1-CMV-Luc or rAd5-CMV-Luc diluted to PBS were administered and needle was withdrawn. The mice were monitored after the procedure to ensure that there was no adverse effect every day until 48 hours after vector administration.

In Vivo Biodistribution.

Forty-eight hours after oral or intraduodenal administration, B6 mouse duodenum (only for oral administration), jejunum without PP (2 cm median part of the small intestine without macroscopically visible PP), ileum without PP (2 cm upstream of the cecum without visible PP), ileal containing PPs (visible PPs observed immediate upstream of the cecum), colon (2 cm downstream of the cecum), MLNs, spleen, and liver (only for intraduodenal administration) were isolated, and DNA was purified by a QIAamp DNA blood mini kit (Qiagen, Germantown, Md.) and analyzed by real-time PCR. Tissues were analyzed by hematoxylin and eosin staining, and immunohistochemistry or immunofluorescence for luciferase staining.

Immunohistochemistry.

Luciferase proteins in B6 mouse tissues after oral and intraduodenal administrations were detected by immunohistochemistry with a 1:100 dilution of a primary goat anti-luciferase (Promega, Madison, Wis.) antibody and a 1:200 dilution of secondary polyclonal rabbit anti-goat IgG-HRP (Dako, Glostrup, Denmark). Tissues were fixed with 4% paraformaldehyde (PFA) in PBS, embedded in paraffin wax, sectioned at 3 μm, and stained sequentially with hematoxylin and eosin (H&E) staining as well as immunohistochemistry for luciferase proteins. Immunohistochemistry was performed with an EnVision+ system-HRP/DAB (Dako). Formalin-fixed paraffin-embedded tissue sections were sequentially deparaffinized, rehydrated, boiled in 0.1 M citrate buffer (pH 6.0, Dako) for antigen retrieval, and blocked for non-specific activity with 1% bovine serum albumin (Sigma-Aldrich, St. Louis, Mo.) and protein block serum-free (Dako). Incubation with primary antibody was performed overnight at 4° C. After a brief rinse in PBS with 0.1% Tween20, the sections were incubated with secondary antibody for 30 minutes and with DAB+ substrate-chromogen solution (Dako) at room temperature. The slides were mounted in Glycergel Mounting Medium (Dako). The histological findings of mouse tissues were assessed with H&E staining of slides. All stainings were performed in at least two independent experiments. All slides were scanned at ×100, ×200, and ×400 magnification using a Nikon Eclipse TS100 microscope (Nikon, Melville, N.Y.). The primary antibody was omitted on the slides for negative controls, where the signals were not detected.

Immunofluorescence Staining.

The cultured cells and frozen B6 mouse tissues for H&E stains were fixed with 4% PFA at room temperature for 10 minutes. The frozen sections (6 μm-10 μm) were cut on a cryostat and prepared for staining experiments. After the evaluation of tissues using H & E stain, the sections were fixed with cold acetone (−20° C.) for 10 minutes. The cells or tissues were then rinsed with PBS, blocked with 1% BSA in 0.1% Tween20-PBS, incubated with the primary monoclonal antibody (Luc, 1:50; Foxp3, 1:50, eBioscience, Inc. San Diego, Calif.) overnight, and followed by incubation with a Tetramethyl Rhodamine Isothiocyanate-conjugated secondary antibody (Jackson ImmunoResearch Laboratories, Inc., West Grove, Pa.) for one hour and FITC-anti-mouse CD11c antibody (eBioscience, Inc. San Diego, Calif.) or FITC isotype control (for negative control) for one hour. Finally, DAPI (Vector Laboratories, Inc. Burlingame, Calif.) was used as a nuclear counterstain. Images were acquired using a confocal spectral imaging microscope system (Nikon). The unstained and secondary antibody only control sections were used to determine the level of background tissue autofluorescence and to identify any potential non-specific binding of the secondary antibodies. Each stain was carried out on at least three individual mice per group and the images in the figures are representative of each group. The numbers of Foxp3+ cells were counted in >10 HPF (×400) per tissues (n=6 in each group, in triplicate).

Isolation of Lymphoctes from Spleen, Liver, and Mesenteric Lymph Nodes.

Splenocytes were prepared for analyses by passing through 100-μm strainer. Erythrocytes were removed using red-blood cells lysis buffer for 5 minutes followed by washes in PBS and passing through 40-μm strainer. Intrahepatic lymphocytes (IHLs) were isolated from livers as follows. After perfusing the portal vein with 5 mL ice-cold PBS, liver tissues were cut into less than 1 mm$^3$ and prepared by washing in ice-cold RPMI1640 (Mediatech, Inc., Manassas, Va.) for removing blood. Tissues from the liver were incubated with 100 U/mL collagenase D and 10 U/mL RNase-free DNase in RPMI1640 for 40 minutes agitated with scissors or swards, followed by passing through 100-μm strainer. Mononuclear cells were prepared by lymphocyte separation medium (Mediatech, Inc.) and passed through 40-μm strainers. The isolated mesenteric lymph nodes (MLNs) were incubated in RPMI1640 with collagenase D and DNase for 30 minutes with agitating with scissors or swards, and passing through 70 μm and 40 μm strainers. Viable splenocytes and lymphocytes were counted using a hemacytometer and trypan blue.

Intracellular Cytokine Staining and Flow Cytometry.

Splenocytes, IHLs, and lymphocytes from MLNs at 14 or 42 days after intraduodenal administration were harvested from B6 mice. In delayed-type hypersensitivity responses analysis, splenocytes were isolated at seven days after subcutaneous Ova challenge. Splenocytes (>1×10$^6$) or lymphocytes (>5×10$^5$) were directly analyzed by flow cytometry (FCM) or placed in culture depends on the analyses.

The Ova-specific CD8+ T cells were analyzed after pro5 MHC Pentamer H-2K$^b$-SIINFEKL (ProImmune Ltd., Oxford, UK) followed by surface staining with anti-CD8a and CD19. The regulatory T cells were identified as CD4+CD25+Foxp3+ cells using Foxp3 Staining Buffer Set (eBioscience, Inc. San Diego, Calif.).

Prior to intracellular cytokine staining, splenocytes (2×10$^6$/mL) or IHLs were incubated with 10 μg/mL of Ova peptide (SIINFKL, H-2K$^b$; ProImmune Ltd., Oxford, UK), Pan02-Ova cell lysate (generated by four freeze-thaw cycles, passed through a 0.22-μm filter, and total protein concentration as determined by a DC protein assay), or 0.1% DMSO and PBS (control) in RPMI 1640 supplemented with 10% FBS, 2 mM L-glutamine, 1 mM sodium pyruvate, and 100 IU/mL penicillin and 100 μg/mL streptomycin for six hours. BD GolgiPlug (BD Biosciences) was added for the last four hours of ex vivo culture. After surface staining with anti-CD3e, CD4, CD8a, or NK1.1 (BD Biosciences), cells were stained with anti-IFN-γ, IL-4, and IL-10 using Cytofix/Cytoperm kit (BD Biosciences, San Jose, Calif.). Over 2×10$^5$ events were aquired on FACSCalibur or LSR11 (BD Biosciences, San Jose, Calif.). Data were analyzed using CellQuest (BD Biosciences, San Jose, Calif.) and FlowJo (TreeStar Inc., Ashland, Oreg.) software. Cells in the lymphocyte gate were used for analysis. As a negative control, cells were stained with isotype controls.

Evaluation of Ova-Specific IgG1, IgG2a and IgE Levels in Serum or Plasma, and IgA in Feces.

Blood samples were drawn from the retro-orbital plexus using heparin- or non-coated glass capillaries, or obtained by cardiac puncture in heparin- or non-coated syringes immediately following sacrifice, and allowed to clot at 37° C. for two hours (for serum). The clots from serum or cells from plasma were removed by centrifuging for 15 minutes at 10000 rpm at 4° C., and the supernatant was stored at −80° C.

Fecal pellet samples were collected and extracted by making a 1/10 suspension (w/v) with PBS plus protease inhibitor. After the suspension samples were vortexed and spun for 10 minutes at 14000 rpm. The supernatant was stored at −80° C.

Sera and feces were tested at 1/10 and 1/50 (for feces) or 1/100 (for sera or plasma) in duplicate. Serum or plasma IgG1, IgG2a and IgE, and fecal IgA concentrations were calculated with controls placed in each enzyme-linked immunosorbent assay plate (Mouse Anti-Ovalbumin IgG1, IgG2a, IgE, or IgA ELISA Kit; Alpha Diagnostic International, Inc., San Antonio, Tex.). The positive controls gave the optical density readouts (>0.3 for sera or plasma, >0.5 for feces). Results are presented as activity units Delayed-Type Hypersensitivity.

The effects of intraduodenally-administered control (PBS), rAd40pΔE1-CMV-Ova, and rAd5ΔE1-CMV-Ova were compared for delayed-type hypersensitivity assay, referred to a previous report (Worbs et al., 2006 J. Exp. Med. 203, 519-527). Two weeks after intraduodenal administration, B6 mice were immunized with a subcutaneous administration of 200 μL PBS/complete Freund's adjuvant emulsion containing 300 μg Ova protein (A-5503, Sigma-Aldrich, St. Louis, Mo.) into the tail base. Fourteen days after immunization, the mice were challenged by subcutaneous administration of 50 μg Ova in 20 μL PBS into the right footpad, while 20 μL PBS without Ova was injected into the left footpat as a control. The swelling was measured in a blinded fashion before subcutaneous administration, as well as 48 and 72 hours after subcutaneous administration with micrometer. Ova-specific swelling was calculated as follows: (right thickness−left thickness)$_{48\ or\ 72\ hours}$−(right thickness−left thickness)$_{0\ hours}$.

Diarrhea Model.

The effect of intraduodenal administration with control (PBS), rAd40pΔE1-CMV-Ova, and rAd5ΔE1-CMV-Ova were compared in allergic diarrhea models, based on a previous report (Brandt et al., 2003 J. Clin. Invest. 112:1666-1677). Two weeks after intraduodenal administration, BALB/c mice were sensitized twice, two weeks apart, with 50 μg Ova in the presence of 1 mg of aluminum potassium sulfate adjuvant (A-7210, Sigma-Aldrich, St. Louis, Mo.) by intraperitoneal administration. Two weeks later, the mice started to receive intragastric administration of 50 mg Ova protein in 250 μL PBS every two days, and it was continued until the two observations of diarrhea in 100% of the control mice. Before each intragastric Ova challenge, mice were deprived of food four hours with the aim of limiting antigen degradation in the stomach. Diarrhea was assessed by visually monitoring mice for up to one hour following intragastric challenge. Mice demonstrating liquid stool was recorded as diarrhea-positive animals.

Systemic Anaphylaxis, Vascular Permeability, and Eosinophil Counts.

After 48 hours following final intragastric challenge in allergic diarrhea models, BALB/c mice were administrated with Ova (100 μg/mice, for systemic anaphylaxis) in Evan's blue (20 mg/kg, for intestinal vascular permeability assay) in PBS (200 μL) intravenously by tail vein injection. Fifteen minutes after intravenously. Ova challenge, blood was drawn from tail vein for analyzing plasma histamine level. Vascular permeability was assessed by Evan's blue dye extravasation as previously described (Green et al., 1998 J. Lab. Clin. Med. 111:173-183; Lange et al., 1994 Scand. J. Gastroenterol. 29:38-46). Eosinophil counts in bone marrow cells were performed using the method based on a previous report (Zhang et al., 2007 Blood 109:4280-4287).

Statistical Analysis.

Data are presented as mean values of at least three independent experiments and error bars indicate the 95% confidence interval. Continuous variables were compared by Mann-Whitney-U test. All P-values were 2-sided, and the type I error rate was fixed at P<0.05. In all figures, asterisks denote statistical significance when comparing indicated groups (*P<0.05, P<0.01, *P<0.001). The picture shown is representative of at least three independent experiments.

Example 6

Cell Lines

The Ad5 E1-expressing human retinoblastic (911) cells (Fallaux et al., 1996 Hum Gene Ther 7(2):215-222), B6 mouse-drived pancreatic adenocarcinoma (Pan02) cells, and B6-derived thyroid lymphoma (EL4, TIB-39; American Type Culture Collection, Manassas, Va.) cells were maintained as previously described in Example 5. For the generation of plasmid encoding chicken ovalbumin (Ova), firefly luciferase (Luc) and GFP reporter fusion gene (LuciGFP, Miura et al., 2007 Gene Ther 14(20):1448-1460), and Msln (1878 bp between 109 and 1986 of GenBank accession sequence NM018857; National Center for Biotechnology Information, NCBI: pMX-Ova-puro, pMX-LuciGFP-puro, and pMX-Msln-puro), DNA fragments encoding Msln were first amplified in RT-PCR using RNA samples from Pan02. Ova-expressing, LuciGFP-expressing, or Msln protein-expressing Pan02 cell lines (Pan02-Ova, Pan02-LuciGFP, or Pan02-Msln) were generated by transducing Pan02 with pMX-Ova-puro, pMX-LuciGFP-puro, or pMX-Msln-puro, respectively, using Lipofectamine 2000 (Invitrogen, Carlsbad, Calif.), selected and maintained by puromycin (2 μg/mL), as previously described in Example 5. Individual stable clones were established using limited dilution methods. Msln protein expression in Pan02-Msln was evaluated by western blot. GFP expression in Pan02-LuciGFP and Msln protein expression in Pan02-Msln were observed by flow cytometry and immunofluorescence. Luc expression in Pan02-LuciGFP was detected by luciferase activity assay.

RNA Extraction and Real-Time Reverse-Transcription PCR Assay.

Total RNA was isolated from the cell pellets using an RNeasy mini kit (Qiagen, Germantown, Md.). Contaminating DNA was removed by RNase-free DNase (Qiagen, Germantown, Md.). One and a half micrograms of total RNA was reverse transcribed using an Omniscript RT kit (Qiagen, Germantown, Md.) with random hexamers (Applied Biosystems, Carlsbad, Calif.). Msln and GAPDH mRNAs were analyzed by RT-qPCR using the QuantiTect SYBR green PCR kit (Qiagen, Germantown, Md.) in an ABI sequence detection system (ABI PRISM 7400, Applied Biosystems, Carlsbad, Calif.) and each experiment was conducted in triplicate. The relative mRNA levels were normalized to GAPDH mRNA. Table 5 shows the primers for Msln and GAPDH. PCR-cloned Msln and GAPDH were used as copy number standards. Template-negative samples served as controls for RT-qPCR and were always sub-detectable.

TABLE 5

| Assay | Primer | Location[a] | Sequence (5' to 3') |
|---|---|---|---|
| RT-qPCR | Mouse mesothelin mRNA | F 778-798 | GCAGTCAGGGAGGTTCTGAGG (SEQ ID NO: 19) |
|  |  | R 846-826 | GGTGGAGACTGACCACTTCGA (SEQ ID NO: 20) |
| RT-qPCR | Mouse GAPDH mRNA | F 311-335 | GGTGCTGAGTATGTCGTGGAGTCTA (SEQ ID NO: 21) |
|  |  | R 407-388 | CGGAGATGATGACCCGTTTG (SEQ ID NO: 22) |

[a]The nucleotide positions of mesothelin mRNA and GAPDH mRNA, respectively, are based on GenBank (NCBI) accession sequence NM018857, and M32599. F, Forward; R, Reverse; RT-qPCR, real-time reverse-transcription PCR.

Mouse Mesothelin Expression Ad Vector Production.

rAd40-Msln was generated using a rescue plasmid, which was inserted homology regions of Ad40-left and right-ends and CMV-promoter-driven Msln, built by transfection to 911, and produced according to the methodology as previously described (40). rAd40-Msln was titered with optical density at 260 nm ($OD_{260}$; virus particle, VP; $1.13\times10^{12}$ VP), and plaque-forming units (PFU; median (interquartile range) of three independent experiments, 7.40 (7.10-7.70)$\times10^6$ PFU/mL) and tissue culture infectious dose 50 (TCID50; 1.25 (1.15-1.34)$\times10^8$ TCID50/mL), and tested for contamination by PCR as previously described (Yamasaki S, Miura Y, Brown E, Davydova J, Vickers S M, Yamamoto M. A single oral administration of human adenovirus 40 vaccine against allergy and anaphylaxis. in press).

Mice.

All animal experiments were conducted with approval from the Institutional Animal Care and Use Committee, University of Minnesota (Minneapolis, Minn.). In all cases, 6-7-week-old female B6 mice (Harlan Laboratories, Madison, Wis.) were utilized.

Intravenous Administration.

Intravenous administration was accomplished with 100 µL PBS (control), or $10^{10}$ VP of rAd40-Luc, rAd40-Ova, rAd40-Msln, rAd5-Luc or rAd5-Ova diluted 100 µL PBS using a 29½-gauge needle into the tail vein. Mice were monitored and observed every day until sacrifice, and ensured that there was no adverse effect.

DNA Extraction and Real-Time PCR-Based Assay.

Viral DNA was purified by a QIAamp DNA blood mini kit (Qiagen, Germantown, Md.) from tissues surgically excised from mice. In order to compare the DNA copy numbers among rAd, previously published primers for luciferase reporter gene and mouse GAPDH were used in real-time PCR analysis by SYBR green method. PCR-cloned luciferase reporter and mouse GAPDH fragments were used as copy number standards. The lower limit of relative luciferase reporter DNA was determined to be one luciferase reporter DNA copy per $10^3$ GAPDH DNA copies based on control results.

Western Blot.

Cell pellets were lysed with sample buffer (0.125 M Tris-HCl, pH 6.8, 2% SDS, 5% β-mercaptoethanol, 10% glycerol) plus protease inhibitor (Complete protease inhibitor cocktail EDTA-free mini tablet, Roche Applied Science, Mannheim, Germany) for 30 minutes on ice with gentle vortexing. After homogenization on ice by multiple passages through a 26-gauge needle, cellular debris was removed by centrifugation (14000 rpm, 10 minutes) at 4° C. Subsequent to denature for five minutes at 95° C. (except for the detection of Msln protein), lysates were separated by 10% SDS-polyacrylamide gel electrophoresis and transferred to PVDF membranes (Bio-Rad, Hercules, Calif.). Membranes were blocked for one hour at 4° C. with 5% nonfat dry milk (NFDM) in 0.05% Tween 20-PBS, and probed with primary antibody (mouse monoclonal anti-Ova antibody, 1:100 dilution, 3G2E1D9; Santa Cruz Biotechnology, Inc.; Santa Cruz, Calif.: goat polyclonal anti-Msln antibody, 1:100, D-16; Santa Cruz Biotechnology, Inc., Santa Cruz, Calif.: mouse monoclonal anti-beta-actin antibody, 1:10000, AC-15, Sigma-Aldrich, St Louis, Mo.), diluted in 0.05% Tween20-PBS (with 5% NFDM for the detection of Msln protein) overnight at 4° C. Membranes were incubated with a horseradish peroxidase conjugated sheep anti-mouse antibody (GE Health, Piscataway, N.J.) or donkey anti-goat antibody (Santa Cruz Biotechnology, Inc., Santa Cruz, Calif.) diluted in 0.05% Tween70-PBS (with 5% NFDM for the detection of Msln protein) for one hour at 4° C., developed by chemiluminescence (ECL plus, GE Health), and exposed to KODAK BioMax MR Film (Carestream Health, Inc.; Rochester, N.Y.). Beta-actin was used as an internal control to adjust for differences in the amount of protein loaded in each lane.

Luciferase Activity Assay.

Luciferase protein levels were assessed using a Luciferase assay system (Promega, Madison, Wis.). The results were read with FLUOstar Omega (BMG LABTECH, Durham, N.C.), and readings were normalized to total protein concentration as determined by a DC protein assay (Bio-Rad Laboratories, Inc., Hercules, Calif.).

In Vivo Biodistribution.

After six hours post rAd intravenous, brain, thymus, lung, heart, liver, spleen, kidney, jejunum (10 cm median part of the small intestine without macroscopically visiable PPs), ileum (10 cm upstream of the cecum), colon (10 cm downstream of the cecum), mesenteric lymph nodes, bone marrow, and peripheral blood of B6 mice were isolated, DNA was purified by a QIAamp DNA blood mini kit, and relative luciferase copy number (luciferase reporter DNA copies per GAPDH DNA copies) in the tissues were analyzed by real-time PCR in three independent experiments as previously described. After 48 hours post rAd intravenous, tissues of B6 mice were assessed via luciferase activity assays after three freeze-thaw cycles as manual recommendation.

Analysis of Plasma Levels of Cytokines and Amino Transferases.

Blood samples were obtained by cardiac puncture in heparin-coated syringes immediately following sacrifice. Cells from plasma were removed by centrifuging for 15 minutes at 10000 rpm at 4° C., and the supernatant was stored at −80° C. To analyze the plasma levels of cytokines, mouse IL-6 and TNF-α ELISA (eBioscience, Inc. San Diego, Calif.) was used according to the manufacturer's protocol. To analyze plasma levels of ALT, ALT activity assay kit (BioVision, Inc., Milpitas, Calif.) was used according to the manufacturer's protocol. Plasma samples obtained from at least three mice for each rAd were analyzed in duplicate.

Intracellular Cytokine Staining and Flow Cytometry.

Cell lines or tumor cells harvested from mice were analyzed by PE-labeled anti-Msln antibody (295D, Molecular & Biological Laboratories, Nagoya, Japan) followed by dead cell staining with 7-AAD (BD Biosciences, San Jose, Calif.).

Splenocytes were prepared by passing through 100-µm strainer. Erythrocytes were removed using red-blood cells lysis buffer for five minutes followed by washes in PBS and passing through 40-µm strainer. Viable splenocytes and lymphocytes were counted using a hemacytometer and trypan blue.

Splenocytes ($>1\times10^6$) were directly analyzed by flow cytometry or placed in culture, depending on the analysis. Ova-specific CD8+ T cells were analyzed after pro5 MHC Pentamer H-$2K^b$-SIINFEKL (ProImmune Ltd., Oxford, UK) followed by surface staining with anti-CD8a and CD19.

Prior to intracellular cytokine staining, splenocytes ($2\times10^6$/mL) were incubated with 10 µg/mL of Ova peptide (SIINFKL, H-$2K^b$; ProImmune Ltd., Oxford, UK), Pan02-Ova, -LuciGFP, or -Msln cell lysate (generated by four freeze-thaw cycles, passed through a 0.22-µm filter, and total protein concentration as determined by a DC protein assay), or 0.1% DMSO and PBS (control) in RPMI 1640 supplemented with 10% FBS, 2 mM L-glutamine, 1 mM sodium pyruvate, and 100 IU/mL penicillin and 100 µg/mL streptomycin for six hours. BD GolgiPlug (BD Biosciences, San Jose, Calif.) was added for the last four hours of ex vivo culture. After surface staining with anti-CD3e, CD4, CD8a, or NK1.1 (BD Biosciences, San Jose, Calif.), cells were stained with anti-IFN-γ, IL-4, and IL-10 using Cytofix/Cytoperm kit (BD Biosciences, San Jose, Calif.).

Over $2\times10^5$ events were aquired on FACSCalibur or LSRII (BD Biosciences, San Jose, Calif.). Data were analyzed using CellQuest (BD Biosciences, San Jose, Calif.) and FlowJo (TreeStar Inc., Ashland, Oreg.) software. FSC/SSC gates were used for analysis as the 7-AAD-negative population for cell lines or lymphocyte gate for splenocytes. As a negative control, cells were stained with isotype controls.

In Vivo Bioluminescence in Tumor Models.

Tumors were established in B6 mice by subcutaneous or orthotopic injection of Pan02-LuciGFP cells ($5\times10^5$ or $2.5\times10^5$ viable cells per mouse, respectively) into the flank or the head from the tail of pancreas using a 29½-gauge needle after a small laparotomy performed exposing the inferior pole of the spleen and tail of the pancreas, which were externalized through the wound. The skin and abdominal musculature were closed with 4-0 Nylon sutures. Mice were monitored and weighed every three days. Tumor growth was monitored with in vivo bioluminescence imaging every week after tumor inoculation. Briefly, mice were anaesthetized with isofluorane (Hospira, Inc., Forest Lake, Ill.) injected intraperitoneally with 15 mg/mL D-luciferin (Molecular Imaging Products Co., Bend, Oreg.) and imaged 10 minutes later with a charge coupled device camera (IVIS 100, Caliper Life Sciences, Inc., Hopkinton, Mass.). After acquiring a grey scale photograph, a bioluminescent image was obtained using 20 cm field of view, binning factor of 8, 1/f stop and open filter and used 1 minute long exposure. Regions of interest (ROIs) were defined manually, signal intensities were calculated using the Living Image software (Caliper Life Sciences, Inc., Hopkinton, Mass.) and expressed as photons per second. Background photon flux was defined from a ROI drawn over a control mouse where no Pan02-LuciGFP had been administered (abdominal bioluminescent total flux $<1\times10^6$ photons/sec).

Isolation of Tumor Cells from Mice.

Tumor cells were cultured in RPMI1640 with 200 U/mL collagenase D (Invitrogen, Life Technologies Corp., Carlsbad, Calif.) and 10 U/mL RNase-free DNase (Promega, Madison, Wis.) for 150 minutes by agitating with scissors or swards, and passing through 100- and 40-μm strainers. Viable tumor cells were counted using a hemacytometer and trypan blue.

Immunofluorescence Staining for Mouse Mesothelin Expression.

For immunofluorescence, cultured cells and frozen tissues for H & E stains were fixed with 4% paraformaldehyde/phosphate buffered saline (PFA/PBS) at room temperature for 10 minutes. Frozen sections (6 μm-10 μm) were cut on a cryostat and prepared for staining experiments. After the evaluation of tissues using H & E stain, sections were fixed with cold acetone (−20° C.) for 10 minutes. Cells or tissues were rinsed with PBS, blocked with 1% BSA in 0.1% Tween20-PBS, incubated with the primary monoclonal antibody (Msln, 1:50) overnight, and followed by incubation with a Tetramethyl Rhodamine Isothiocyanate-conjugated secondary antibody (Jackson ImmunoResearch Laboratories, Inc., West Grove, Pa.) for one hour. Finally, DAPI (Vector Laboratories, Inc. Burlingame, Calif.) was used as a nuclear counterstain. Images were acquired using a confocal spectral imagingmicroscope systems (Nikon). The unstained and secondary antibody only control sections were used to determine the level of background tissue autofluorescence and to identify any potential non-specific binding of the secondary antibodies.

In Vivo Cytotoxic T-Cell Assay.

B6 splenocytes ($5\times10^6$/mL) were incubated for 90 minutes at 37° C. with or without 1 μg/mL of OVA peptide (SIINFKL, SEQ ID NO:23, H-2Kb; ProImmune Ltd., Oxford, UK) and labeled for 10 minutes at 37° C. with carboxyflurescein diacetate succinimidyl diester (CFSE, Molecular Probes, Life Technologies Corp., Carlsbad, Calif.) at 5 μM ($CFSE^{high}$, peptide-labeled splenocytes) or 0.5 μM ($CFSE^{low}$, splenocytes without peptide). B6 mice at 14 days after intravenous administration with PBS (control) or $10^{10}$ VP of rAd40-Ova and rAd5-CMV-Ova were injected intravenously with $2.5\times10^6$ cells of each fraction. Splenocytes were isolated 20 hours later, and analyzed by FCM. The ratio between the percentage of pulsed cells ($CFSE^{high}$) and the percentage of the unpulsed cells ($CFSE^{low}$) was calculated to determine cell cytotoxicity. Over $1\times10^6$ events were aquired on FACSCalibur (BD Biosciences, San Jose, Calif.). Data were analyzed using CellQuest (BD Biosciences, San Jose, Calif.) and FlowJo (TreeStar Inc., Ashland, Oreg.) software. CD3e+CD8a+ cells in the lymphocyte gate were used for analysis.

Tumor Challenge Study in Subcutaneous Tumor Models.

At 14 days after intravenous administration with PBS, or $10^{10}$ VP of rAd40-Ova, or rAd5-Ova, Pan02-Ova or Pan02-LuciGFP cells ($5\times10^5$ viable cells per mouse) were inoculated subcutaneously into the flank of B6 mice. Mice were monitored and weighed every three days. Tumor growth was monitored with fine calipers and tumor volumes were estimated from 2-dimensional measurements: tumor volumes $(mm^3)=(A\times B^2)/2$, where A and B are the tumor length and width in (mm), respectively. The larger diameter is considered the length, and the smaller diameter is considered the width. Thirty days after tumor inoculation, mice were sacrificed, and peripheral blood, tumor and splenocytes were extracted.

Tumor Challenge Study in Orthotopic Tumor Models.

At 14 days after intravenous administration with PBS, or $10^{10}$ VP of rAd40-Ova, or rAd5-Ova, Pan02-LuciGFP cells ($2.5\times10^5$ viable cells per mouse) were inoculated in the head from the tail of pancreas. Mice were monitored and weighed every three days. Tumor growth was monitored with bioluminescence imaging every week after tumor inoculation. Four weeks after tumor inoculation, mice were sacrificed, and peripheral blood, tumor and splenocytes were extracted.

Statistical Analysis.

Data are presented as mean values of at least three independent experiments and error bars indicate 95% CI. Continuous variables were compared by Mann-Whitney-U test. All P-values were 2-sided, and the type I error rate was fixed at $P<0.05$. In all figures, asterisks denote statistical significance when coparing indicated groups (*$P<0.05$ and $P<0.01$, *$P<0.001$). The picture shown is representative of at least three independent experiments.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A viral particle comprising a genetically modified polynucleotide, the genetically modified polynucleotide comprising:
    an Ad40-based polynucleotide comprising a genetic modification that comprises:
        a partially deleted Ad40 E1 coding region; or
        a deletion of a regulatory polynucleotide sequence that is required for expression of the Ad40 E1 coding region; and
    a heterologous polynucleotide.

2. The viral particle of claim 1 wherein the heterologous polynucleotide comprises a polynucleotide that encodes a polypeptide effective for treating a medical condition.

3. The viral particle of claim 2 wherein the medical condition comprises a cancer.

4. The viral particle of claim 2 wherein the medical condition comprises an infectious disease.

5. The viral particle of claim 2 wherein the medical condition comprises an inflammatory disease.

6. The viral particle of claim 1 wherein the heterologous polynucleotide comprises a therapeutic polynucleotide.

7. The viral particle of claim 1 wherein the heterologous polynucleotide comprises a prophylactic polynucleotide.

8. A composition comprising the viral particle of claim 1 and a pharmaceutically acceptable carrier.

9. The composition of claim 8 further comprising an enteric coating.

* * * * *